(12) United States Patent
Rovera et al.

(10) Patent No.: US 6,221,635 B1
(45) Date of Patent: Apr. 24, 2001

(54) METHODS FOR SOLID-PHASE AMPLIFICATION OF DNA TEMPLATE (SPADT) USING MULTIARRAYS

(75) Inventors: Giovanni Rovera; Sunil Mukhopadhyay, both of Bryn Mawr, PA (US)

(73) Assignee: The Wistar Institute, Philadelphia, PA (US)

( * ) Notice: Subject to any disclaimer, the term of this patent is extended or adjusted under 35 U.S.C. 154(b) by 0 days.

(21) Appl. No.: 09/306,290

(22) Filed: May 6, 1999

(51) Int. Cl.[7] .............................. C12P 19/34; C12Q 1/70; C12Q 1/68
(52) U.S. Cl. ................................. 435/91.2; 435/5; 435/6
(58) Field of Search .................... 435/91.2, 6, 5

(56) References Cited

U.S. PATENT DOCUMENTS

| | | | |
|---|---|---|---|
| 4,415,732 | 11/1983 | Caruthers et al. | 435/6 |
| 4,458,066 | 7/1984 | Caruthers et al. | 536/25.34 |
| 4,725,677 | 2/1988 | Köster et al. | 536/25.34 |
| 4,980,460 | 12/1990 | Molko et al. | 536/26.71 |
| 5,641,658 | 6/1997 | Adams et al. | 435/91.2 |
| 5,691,146 | 11/1997 | Mayrand | 435/6 |
| 5,698,400 | * 12/1997 | Cotton | 435/6 |

OTHER PUBLICATIONS

Erker et al. Journal of Virological Methods 70(Jan. 1998) 1–5.*
Innis et al. PCR Protocols, Academic Press, 1990, p. 6.*
He et al. Biotechniques, vol. 17, No. 1 (1994) pp. 82–87.*
Agulnick et al., 1993, J. Gen. Virol. 74:1003–1009.
Anilionis et al., 1981, Nature 294:275–278.
Beaucage and Iyer, 1992, Tetrahedron 48:2223–2311.
Breslauer et al., 1986, Proc. Natl. Acad. Sci. U.S.A. 83:3746–3750.
Caetano–Anolles, 1996, Nature Biotech. 14:1668–1674.
Castellino, 1997, Genome Res. 7:943–946.
Chamberlain et al., 1988, Nucleic Acids Res. 16:11141–11156.
Church and Gilbert, 1984, Proc. Natl. Acad. Sci. USA 81:1991–1995.
Editorial, 1998, Nature Genet. 18:195–197.
Espelund et al., 1990, Nucleic Acids Res. 18:6157–6158.
Holmberg et al., 1992, Mol. Cell. Probes 6:201–208.
Hultman et al., 1989, Nucleic Acids Res. 17:4937–4946.
Jakobsen et al., 1990, Nucleic Acids Res. 18:3669.
Kricka, 1998, Nature Biotechnology 16:513–514.
Kuribayashi–Ohta et al., 1993, Biochim. Biophys. Acta 1156:204–212.
Lockhart et al., 1996, Nature Biotechnology 14:1675–1680.
Lockley et al., 1997, Nucleic Acids Res. 15:1313–1314.
Lowe et al., 1990, Nucleic Acids Res. 18:1757–1761.
Mar–Aguilar et al., 1998, Clin. Lab. Haematology 20:221–224.
Ramsay, 1998, Nature Biotechnology 16:40–44.
Reed and Mann, 1985, Nucleic Acids Res. 13:7207–7221.
Rouwendal et al., 1993, Biotechniques 15:68–76.
Saiki et al., 1989, Proc. Natl. Acad. Sci. U.S.A. 86:6230–6234.
Saiki et al., 1985, Science 230:1350–1354.
Skryabin et al., 1990, Nucleic Acids Res. 18:4289.
Tagle et al., 1993, Nature 361:751–753.
Varadaraj and Skinner, 1994, Gene 140:1–5.
Wahlberg et al., 1990, Proc. Natl. Acad. Sci. U.S.A. 87:6569–6573.
White et al., 1989, Trends Genet. 5:185–189.
Wu et al., 1994, Nucleic Acids Res. 22:3257–3258.
Yamada et al., 1989, Proc. Natl. Acad. Sci. U.S.A. 86:5123–5127.
Zietkewicz et al., 1994, Genomics 20:176–183.

* cited by examiner

*Primary Examiner*—Jeffrey Fredman
*Assistant Examiner*—Juliet C. Einsmann
(74) *Attorney, Agent, or Firm*—Akin, Gump, Strauss, Hauer & Feld, L.L.P.

(57) ABSTRACT

The present invention relates to a novel method of detecting specific nucleic acids in a biological sample using solid-phase amplification of DNA template (SPADT) using multiarrays.

19 Claims, 22 Drawing Sheets

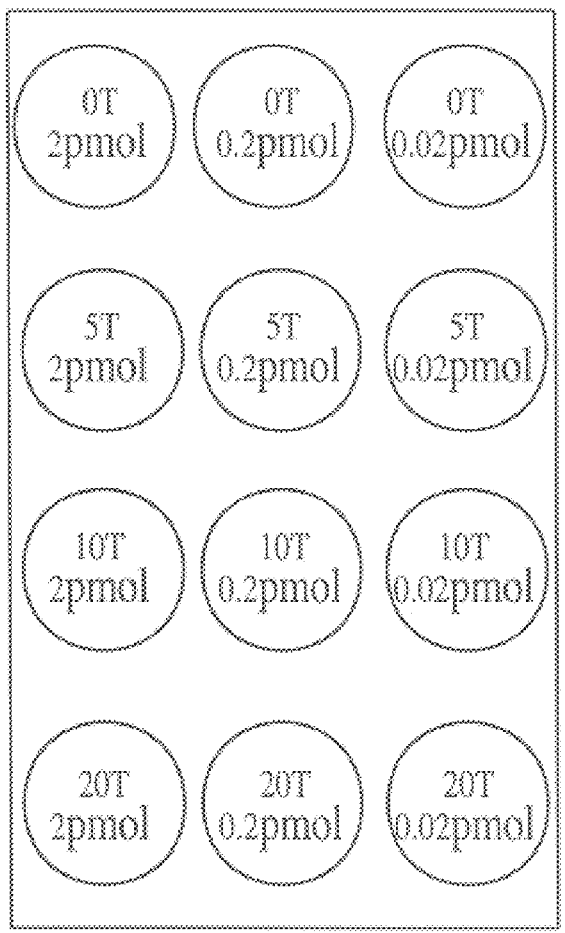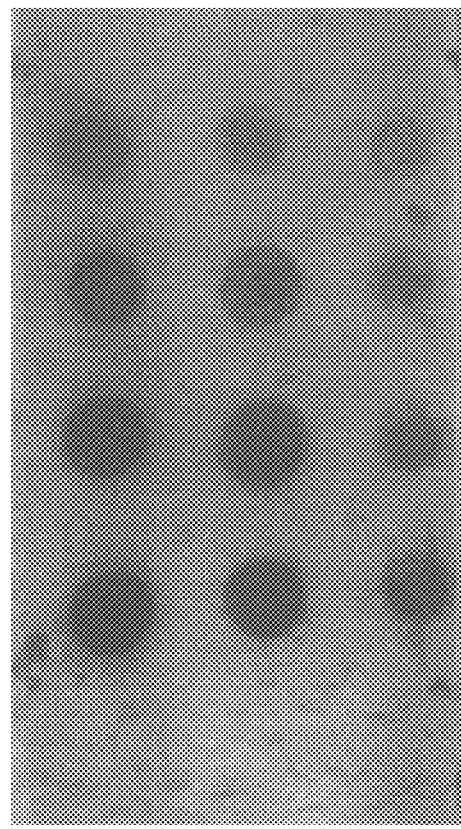
Fig. 1A                    Fig. 1B

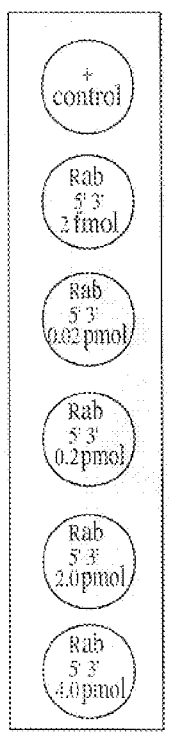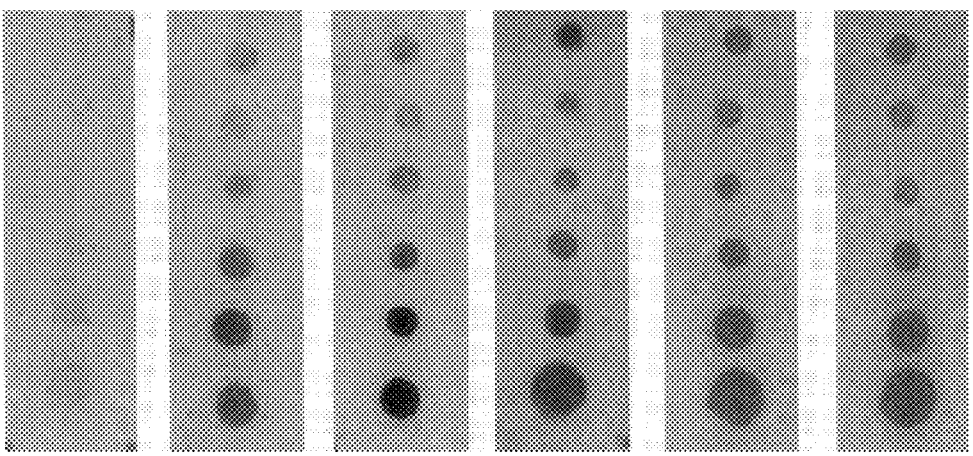
Fig. 2A  Fig. 2B  Fig. 2C  Fig. 2D  Fig. 2E  Fig. 2F  Fig. 2G

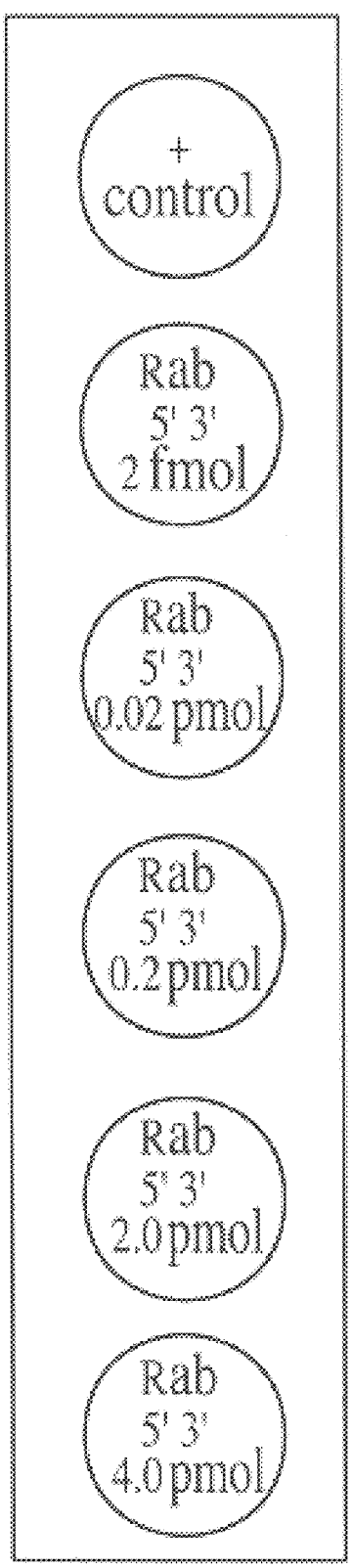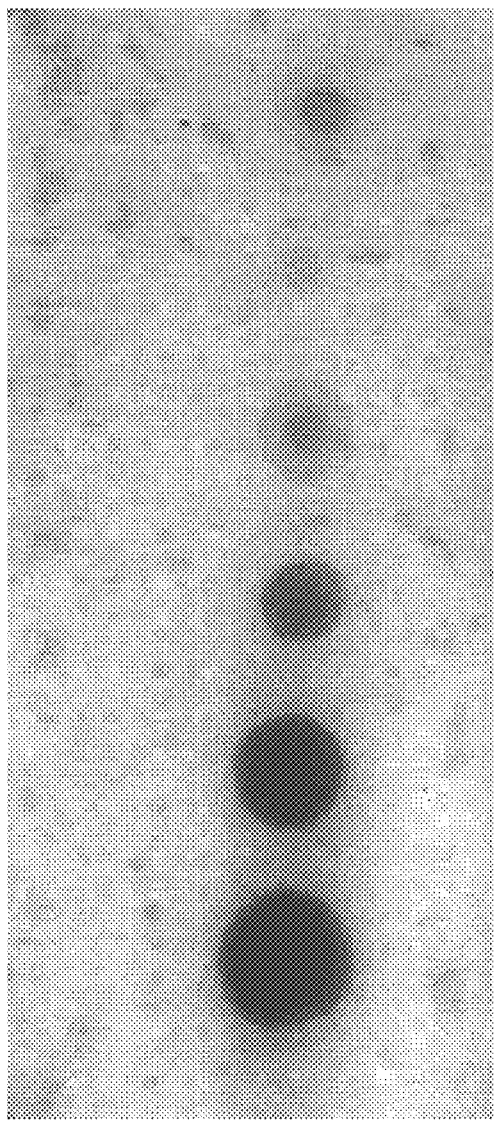
Fig. 3A
Fig. 3B

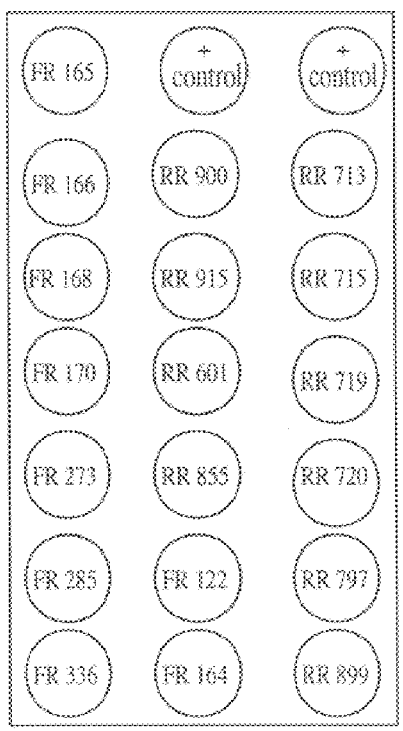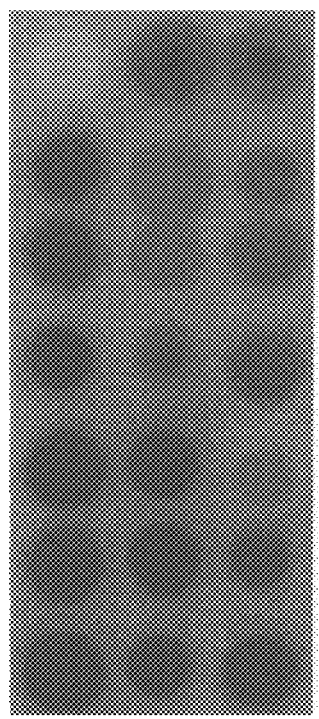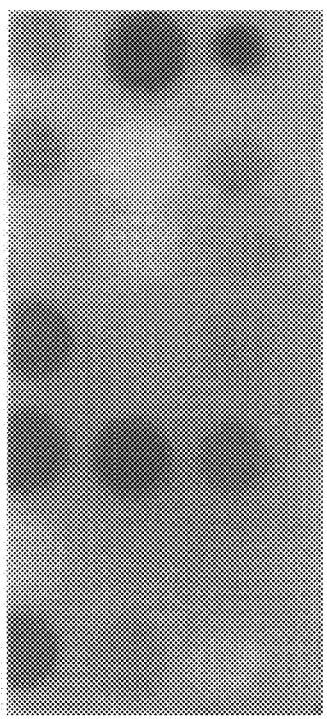
Fig. 4A-1  Fig. 4A-2  Fig. 4A-3

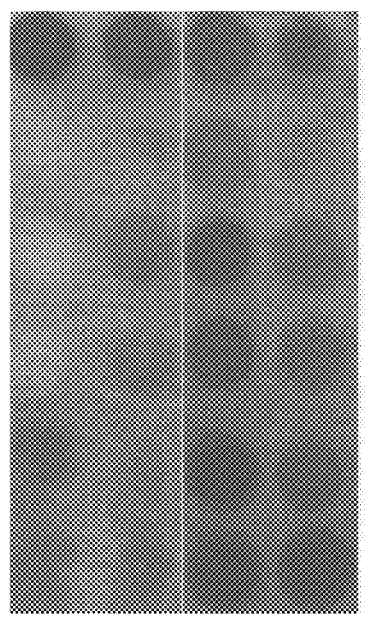
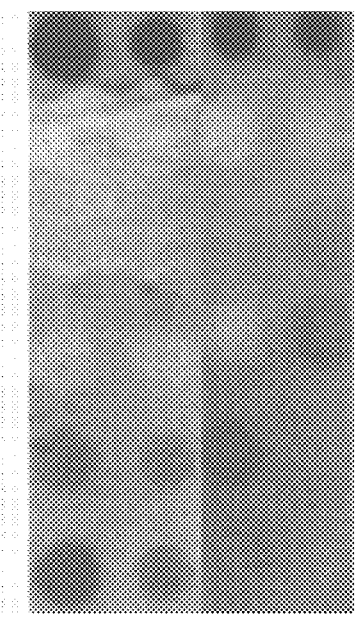
Fig. 5A-1    Fig. 5A-2    Fig. 5A-3

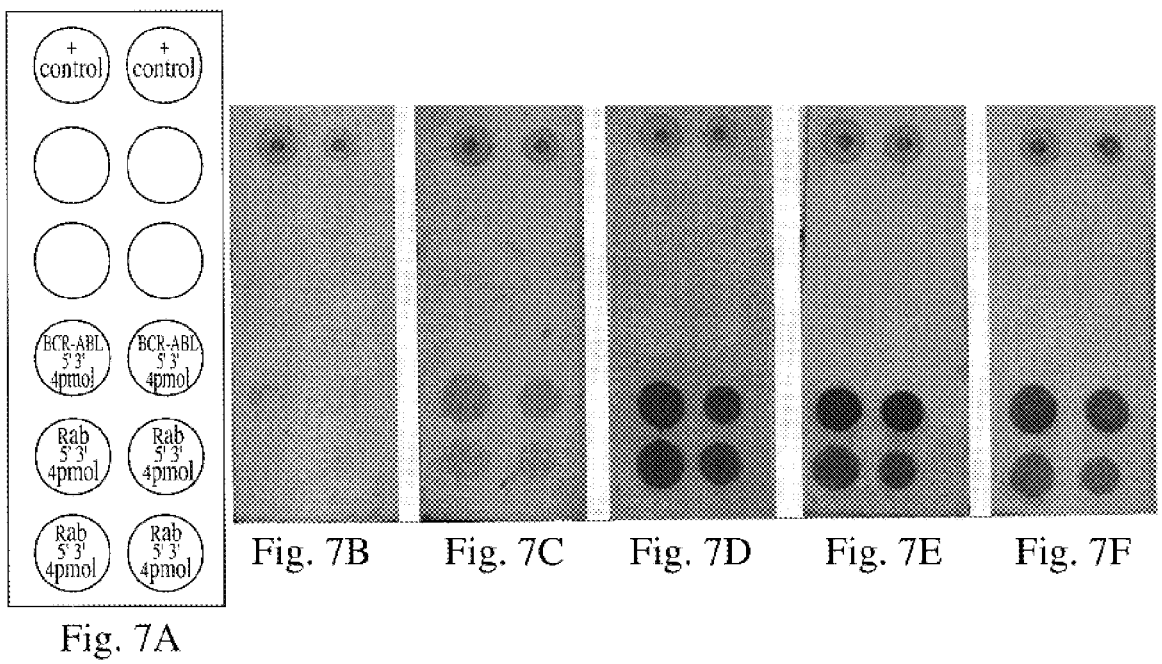

Fig. 8A
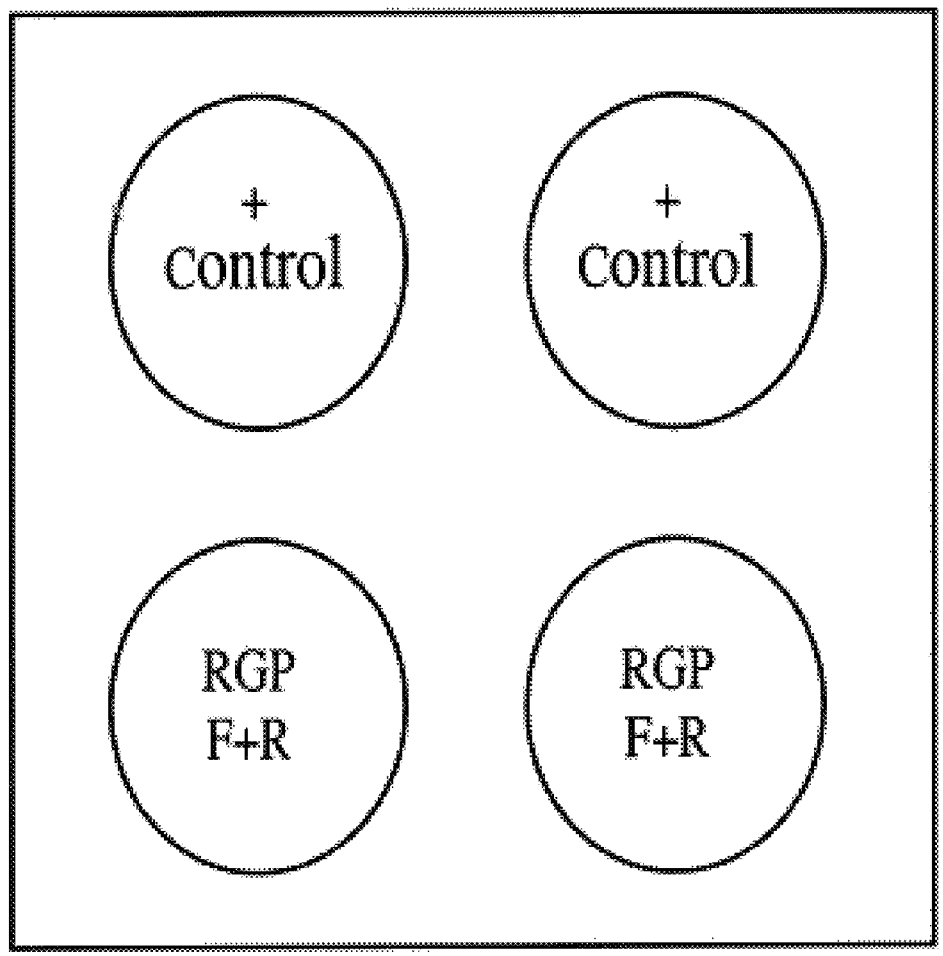
Fig. 8B    Fig. 8C
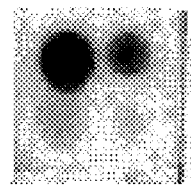 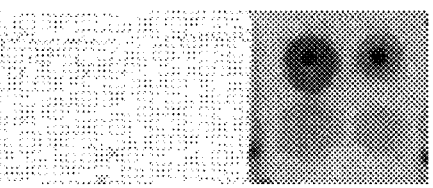

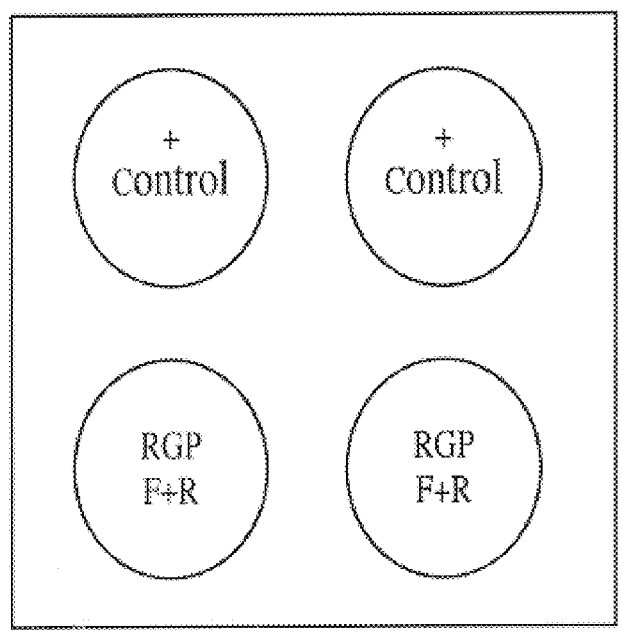
Fig. 9A
Fig. 9B  Fig. 9C  Fig. 9D  Fig. 9E
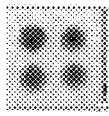   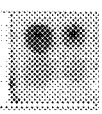

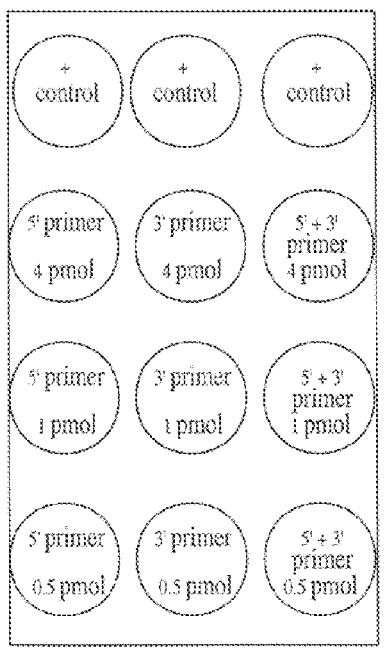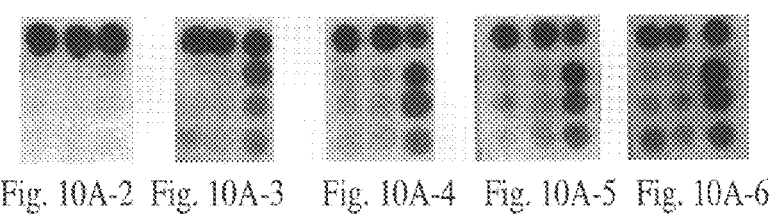
Fig. 10A-1  Fig. 10A-2  Fig. 10A-3  Fig. 10A-4  Fig. 10A-5  Fig. 10A-6

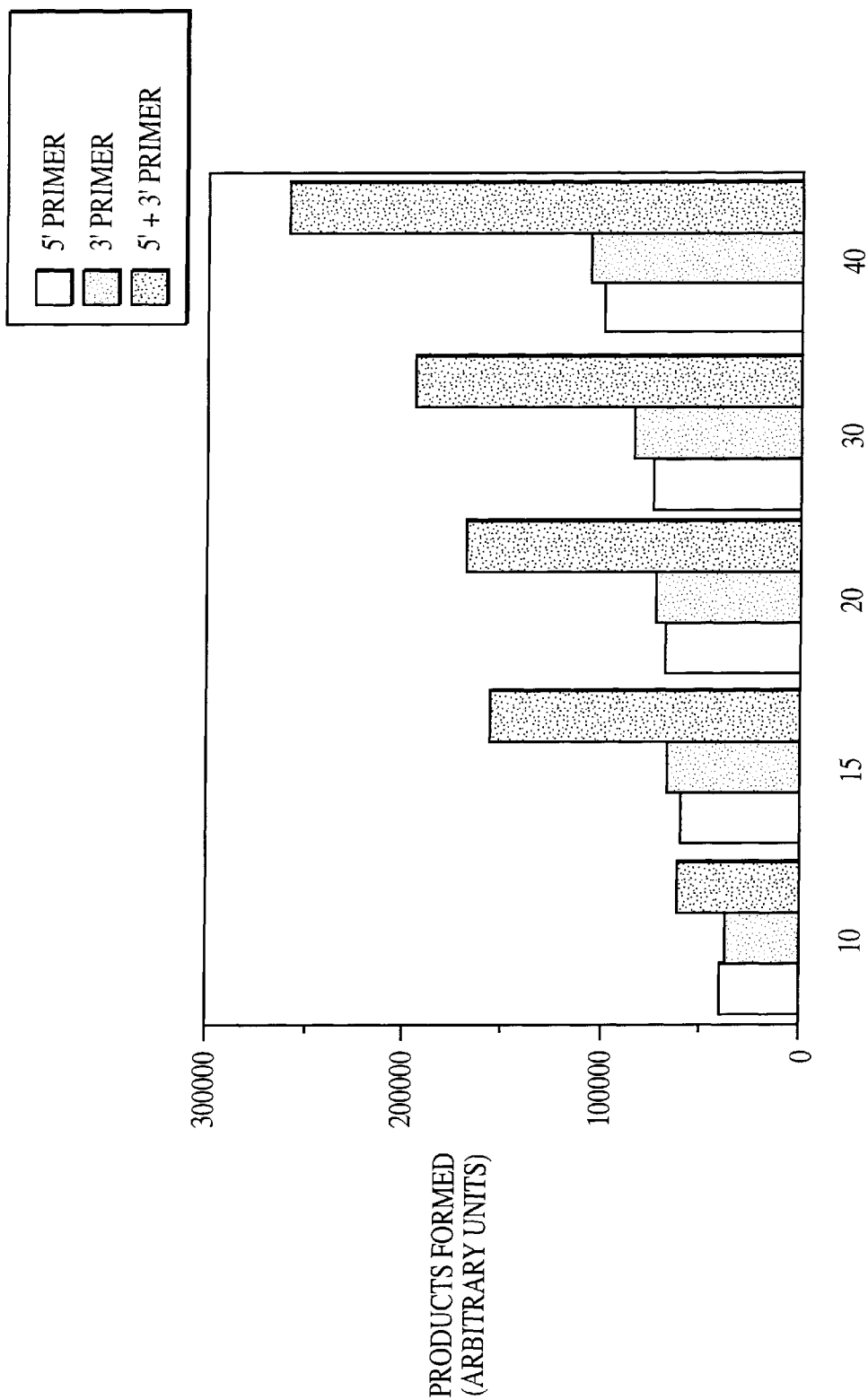

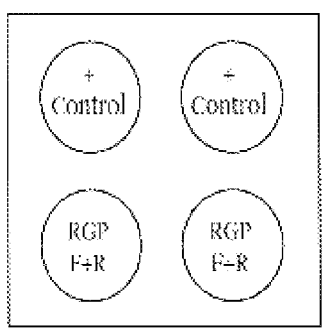
Fig. 12A
Fig. 12B-1    Fig. 12B-2    Fig. 12B-3    Fig. 12B-4
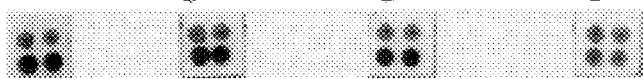
Fig. 12C-1    Fig. 12C-2    Fig. 12C-3    Fig. 12C-4
Fig. 12D-1    Fig. 12D-2    Fig. 12D-3    Fig. 12D-4

METHODS FOR SOLID-PHASE AMPLIFICATION OF DNA TEMPLATE (SPADT) USING MULTIARRAYS

BACKGROUND OF THE INVENTION

The ability to interrogate an unknown, small DNA sample with a relatively large number of questions and obtain a rapid yes/no complement of answers is highly desirable in many areas of molecular diagnostics. Developments in DNA and RNA amplification technology have enabled the design of very sensitive, high throughput methods (Saiki et al., 1985, Science 230:1350–1354). Polymerase chain reaction (PCR) amplification has been used to scan nucleic acid sequences for profiling or fingerprinting purposes using either predictable or arbitrary primers (Caetano-Anolles, 1996, Nature Biotech. 14:1668–1674). When predictable primers are used, the presence and distribution of repeated sequences in a genomic sample can be identified. Utilizing random primers, a multiplicity of anonymous sites in nucleic acid templates are scanned producing fingerprints or arbitrary collections of amplified products, giving rise to a specific profile of the genome being analyzed.

The possibility of interrogating an uncharacterized DNA sample for the presence of scarce copies of foreign DNA, or to determine whether it contains unique members of a large gene family or one of many possible genetic rearrangements is not yet satisfactorily resolved. Multiplex PCR (Chamberlain et al., 1988, Nucleic Acids Res. 16:11141–11156) could be utilized in theory, but if suffers from several limitations, the most serious being the undesirable interactions occurring with the increase in the number of primers in the multiplex PCR reaction. The alternative of carrying out hundreds of PCRs in parallel, each reaction containing primers specific for a defined gene sequence, is overly cumbersome, requiring highly specialized equipment and large amounts of reagents. The use of chips containing microarrays of diagnostic probes is only suitable if the gene of interest is sufficiently abundant in the sample and the procedure involves multiple steps (CDNA synthesis, PCR amplification, hybridization) that makes the procedure cumbersome. A more viable alternative would be to analyze a target DNA template using multiple sets of compartmentalized primer pairs anchored to a solid-phase, but a solid-phase PCR that can exponentially amplify target DNA has not yet been reduced to practice.

Methodologies of DNA template amplification have been developed in which either the nucleic acid template or the oligonucleotide primers are anchored to a solid-phase. In situ PCR wherein the nucleic acid template is immobilized on a nylon membrane, is an example (Skryabin et al., 1990, Nucleic Acids Res. 18:4289). Solid-phase anchored PCR is another example in which primers modified with amino links and coupled to solid-phase like agarose, acrylamide, magnetic beads (Jakobsen et al., 1990, Nucleic Acids Res. 18:36695) or latex beads (Kuribayashi-Ohta et al., 1993, Biochim. Biophys. Acta 1156:204–212) are used for a variety of applications. Such applications include the generation of immobilized cDNA suitable for automated sequencing of single stranded DNA (Hultman et al., 1989, Nucleic Acids Res. 17:4937–4946), the detection of products in automated clinical assays (Holmberg et al., 1992, Mol. Cell. Probes 6:201–208; Wahlberg et al., 1990, Proc. Natl. Acad. Sci. U.S.A. 87:6569–6573), the generation of probes with high specific activity (Espelund et al., 1990, Nucleic Acids Res. 18:6157–6158), the construction of cDNA libraries (Tagle et al., 1993, Nature 361:751–753) and hybrid selection of RNA (Kuribayashi-Ohta et al., 1993, Biochim. Biophys. Acta 1156:204–212). Oligonucleotide probes, crosslinked to nylon, have been used for detection of specific PCR products (Saiki et al., 1989, Proc. Natl. Acad. Sci. U.S.A. 86:6230–6234) and anchored oligonucleotide primers have been used for detection of point mutations (Lockley et al., 1997, Nucleic Acids Res. 25:1313–1314). Other examples of solid-phase approaches are AMP-PCR (Wu et al., 1994, Nucleic Acids Res. 22:3257–3258), and RAMP (Zietkewicz et al., 1994, Genomics 20:176–183) using single anchored microsatellites primers.

Recently, a theoretical version of solid-phase PCR using bound forward and reverse primers and DNA template in solution has been proposed in a "bridge" PCR in a patent by Adams and Kron (U.S. Pat. No. 5,641,658). No data are presently available on whether solid-phase anchored primers are truly able to exponentially amplify a template or instead provide a linear amplification of the target template as the result of repeated primer extensions of the template by forward and reverse primer. In addition, there is no suggestion in the prior art that anchored primers and surface adsorbed DNA template on the same solid-phase could yield specific amplified product. Indeed, in light of the prior art teachings, such results are counterintuitive.

The present invention sets forth novel technology which provides a vast improvement to existing nucleic acid amplification methods and fills a long-felt need in the development of cost-effective and efficient methods of detecting low abundance genetic information in complex genomes.

SUMMARY OF THE INVENTION

The present invention relates to a method of detecting the presence or absence of a specific nucleic acid in a sample comprising DNA. The method comprises performing an amplification reaction, wherein a solid support on which a 5' and a 3' primer are irreversibly bound and the DNA is reversibly bound, is incubated under amplification conditions, and determining whether the specific nucleic acid is amplified, wherein when the specific nucleic acid is amplified, the specific nucleic acid is present in the sample and when the specific nucleic acid is not amplified, the specific nucleic acid is not present in the sample.

In one aspect, the solid support comprises a solid to which the DNA cannot be irreversibly bound upon adding the DNA to the solid support in the absence of any further reaction.

In another aspect, the solid support is selected from the group consisting of a nylon membrane, and a nitrocellulose membrane.

In a preferred embodiment, the solid support is a nylon membrane.

In another aspect, the primers are irreversibly bound to the solid support by UV-crosslinking the primers to the support.

In yet another aspect, the 5' and 3' primers further comprise a poly-thymidine sequence at their 5' ends.

In another aspect, the poly-thymidine sequence comprises from about 15 to about 80 thymidine nucleotides.

In yet another aspect, the 5' and 3' primers comprise a sequence homologous to the sequence of the specific nucleic acid, the primers ranging in length from about 19 nucleotides to about 23 nucleotides.

In yet a further aspect, if the primers are in double stranded form, the thermal melting temperature of the double stranded form of the primers is in the range of about 55° C. to about 65° C.

In a preferred embodiment, the 5' and 3' primers are substantially lacking a GC rich region near the 3' end of the 5' and 3' primers.

In one aspect, the amplification is performed by a reaction selected from the group consisting of a polymerase chain reaction, and a ligase reaction.

In another aspect, the determination of whether the specific nucleic acid is amplified is performed by incorporating a detectable label into the amplified nucleic acid during amplification and detecting the label.

In yet another aspect, the amplification conditions comprise about 2 mM $MgCl_2$ and about 50 mM KCl.

In yet a further aspect, the specific nucleic acid is selected from the group consisting of a nucleic acid comprising a mutation, a nucleic acid comprising a mutation in a cancer gene, and a nucleic acid comprising a sequence present in the genome of an infectious agent.

The invention also includes a method of determining the presence or absence of expression of a specific nucleic acid in a cell. The method comprises reverse transcribing RNA obtained from the cell to produce DNA, performing an amplification reaction, wherein a solid support on which a 5' and a 3' primer are irreversibly bound and the DNA is reversibly bound is incubated under amplification conditions, and determining whether the DNA is amplified, wherein when the DNA is amplified, the specific nucleic acid is expressed in the cell and when the DNA is not amplified, the specific nucleic acid is not expressed in the cell.

The invention also includes a method of determining the presence or absence of a specific RNA molecule in a sample. The method comprises reverse transcribing the RNA to DNA, performing an amplification reaction wherein a solid support on which a 5' and a 3' primer are irreversibly bound and the DNA is reversibly bound is incubated under amplification conditions, and determining whether the DNA is amplified, wherein when the DNA is amplified, the specific RNA is present in the sample, and when the DNA is not amplified, the specific RNA is not present in the sample.

In one aspect, the specific RNA is viral RNA.

The invention further includes a method of designing a primer which amplifies a specific nucleic acid provided the specific nucleic acid is present in a sample comprising DNA. The method comprises:

(a) synthesizing at least one 5' and one 3' primer homologous to the nucleic acid;

(b) performing an amplification reaction wherein a solid support on which the primer is irreversibly bound and the DNA is reversibly bound is incubated under amplification conditions to generate an amplified nucleic acid;

(c) determining the specificity of the primer by comparing the ability of the primer to produce a detectable amount of the amplified nucleic acid in the amplification reaction in the presence or absence of the specific nucleic acid, wherein a detectable amount of amplified nucleic acid in the amplification reaction in the presence of the specific nucleic acid, compared with the absence of a detectable amount of the amplified nucleic acid in the absence of the specific nucleic acid, is an indicator that the primer is specific for amplifying the specific nucleic acid;

(d) comparing the characteristics of the primers of step (c) which are specific for the specific nucleic acid to identify common features shared among the most specific of the primers; and (e) synthesizing an additional primer incorporating the features identified in step (d), thereby designing a primer which amplifies a specific nucleic acid provided the specific nucleic acid is present in a sample comprising DNA.

In one aspect, the comparing step (d) is performed using an algorithm.

BRIEF DESCRIPTIONS OF THE SEVERAL VIEWS OF THE DRAWINGS

FIG. 1, comprising FIGS. 1A and 1B, is an image of a solid-phase multiarray depicting the identification of the optimal length of the oligo dT leader sequence suitable for UV crosslinking to a nylon matrix (FIG. 1B). Oligonucleotide primers containing a 20 mer oligonucleotide coding sequence homologous to a target gene (RGP) were labeled at the 3' end with digoxigenin. A poly dT sequence of different lengths (i.e., 0T, 5T, 10T or 20T) was synthesized at the 5' end of the primers. The primers containing different lengths poly-dT leader sequences were spotted on the nylon membrane at concentrations ranging from 2 pmol to 0.02 pmol (0.02, 02, or 2 pmol); as indicated in FIG. 1A and the primers were crosslinked by UV irradiation (120 $mJ/cm^2$). The bound primers were subjected to 40 cycles of thermocycling at 55° C., 72° C. and 95° C. The amount of oligonucleotides that remained bound to the nylon matrix was assessed using a colorimetric reaction.

FIG. 2, comprising FIGS. 2A–2G, is an image of a solid-phase multiarray depicting the identification of the optimal UV dose for crosslinking poly-dT-containing primers. Forward and reverse primer pairs containing a 20 mer poly-dT leader sequence and 20 mer coding sequence homologous for the RGP gene were bound to the nylon matrix at a final concentration ranging from 2 fmol to 4 pmol/spot (2 fmol, 0.02 pmol, 0.2 pmol, 2.0 pmol, 4.0 pmol) as indicated in FIG. 2A. The primers were then crosslinked by UV irradiation at doses ranging from about 0 to about 200 $mJ/cm^2$, (0 in FIG. 2B, 40 in FIG. 2C, 80 in FIG. 2D, 120 in FIG. 2E, 160 in FIG. 2F, and 200 in FIG. 2G. The efficiency of the UV crosslinked primers to generate an amplification product was assessed by thermocycling 40 times at 55° C., 72° C. and 95° C. in presence of a template DNA (RGP) in solution.

FIG. 3, comprising FIGS. 3A and 3B, is an image of a solid-phase multiarray depicting the optimization of primer concentration on a nylon filter for efficient SPADT. Poly-dT containing forward and reverse primers at concentrations ranging from 2 femtomoles to 4 pmols concentration (as indicated in FIG. 3A) were spotted on a nylon matrix and UV-crosslinked using 120 $mJ/cm^2$ (FIG. 3B). The spots were subjected to template amplification using as template the RGP gene.

FIG. 4A, comprising FIGS. 4A-1, 4A-2, and 4A-3, is an image of a solid-phase multiarray depicting the design of specific and efficient primers for SPADT of the RGP gene. Poly-dT containing forward and reverse primers homologous to the RGP gene were crosslinked to a nylon matrix using UV irradiation (120 $mJ/cm^2$; as indicated in FIG. 4A-1). The nucleic acid sequences of the primers tested are listed in Table 1. The arrays of crosslinked primers were tested for their ability to extend either a specific RGP template (RGP120); FIG. 4A-2 or a non-specific human genomic template (FIG. 4A-3).

FIG. 4B is a graph depicting the quantitation of intensity of signal by RGP-specific primers for the multiarray shown in FIG. 4A.

FIG. 5A, comprising FIGS. 5A-1, 5A-2, and 5A-3, is an image depicting the design of specific and efficient primers for SPADT amplification of the p41 HHV6 gene. A similar approach as the one described in FIG. 4A was utilized to design specific forward and reverse primers for a p41 HHV6 template. Primers containing a 20 mer poly dT sequence and a 20 mer sequence homologous to p41 HHV6 were crosslinked, in the pattern depicted in FIG. 5A-1, to a nylon matrix by UV irradiation (120 mJ/cm$^2$) and the primers were tested for their ability to extend the HHV6 P41 target gene (FIG. 5A-2) or human genomic DNA (FIG. 5A-3). The nucleic acid sequences of the primers are listed in Table 2.

FIG. 5B is a graph depicting the quantitation of intensity of signal by several of the RGP-specific primers shown in FIG. 5A.

FIG. 6, comprising FIGS. 6A and 6B, is an image of a solid-phase multiarray depicting the optimization of the concentration of Taq polymerase used in the PCR reaction mixture to function efficiently to amplify solid phase bound primers (FIG. 6B). Forward (5') and reverse (3') poly T-oligo primers specific for RGP and other irrelevant primers (E6, BCR, ABL) were crosslinked, in the pattern depicted in FIG. 6A, to a nylon strip. RGP template (40 ng) was added to filters at a final concentration of 2.5 U/100 μl (1 μl), 5U/100 μl (2 μl), and 100/100 μl (4 μl).

FIG. 7, comprising FIGS. 7A–7F, is an image of a solid-phase multiarray depicting the effect of varying concentrations of Triton X100 detergent (0.01% in FIG. 7B, 0.05% in FIG. 7C, 0.1% in FIG. 7D, 0.5% in FIG. 7E, and 1.0% in FIG. 7F). A similar experiment as the one described in FIG. 6 was carried out using Triton X-100 in the reaction buffer at final concentrations ranging from 0.01% to 1%. The amplification products were examined on the solid phase matrix, in the pattern depicted in FIG. 7A, as well as in the solution buffer to rule out whether any leaking of the primers had occurred.

FIG. 8, comprising FIGS. 8A, 8B, and 8C, is an image of a solid-phase multiarray, in the pattern depicted in FIG. 8A depicting the effect of the addition of fresh Taq polymerase during SPADT amplification. A similar experiment as the one described in FIG. 6 was performed with the addition of fresh Taq DNA polymerase at the 25th PCR cycle. The PCR was carried out for a total of 40 cycles. FIGS. 8B depicts results obtained using 1 pg RGP and 100 ng human DNA template.

FIG. 9 comprising FIGS. 9A–9E, is an image of a solid-phase multiarray, in the pattern depicted in FIG. 9A depicting the optimization of buffer composition for efficient amplification of DNA templates by use of various concentrations of DMSO to increase specificity of template amplification. FIG. 9B depicts results obtained using 10 pg RGP DNA template. FIG. 9C depicts results obtained using 10 pg RGP and 100 ng human DNA template. FIG. 9D depicts results obtained using 1 pg RGP DNA template. FIG. 9E depicts results obtained using 1 pg RGP and 100 ng human DNA template.

FIG. 10A comprising FIGS. 10A-1 through 10A-6, is an image of a solid-phase multiarray depicting the amplification of DNA template in solution. Arrays of individual forward and reverse RGP specific primers or matching forward and reverse primer pairs at concentrations ranging from 4pmol (second row from the top), 1 pmol (third row from the top), to about 0.5 pmol (fourth row from the top) were UV crosslinked to Hybond Nylon, in the pattern depicted in FIG. 10A-1. The arrays were thermocycled at 55° C., 72° C. and 95° C. in the presence of 10 nanogram of RGP DNA template in solution buffer and the samples were examined after 10(FIG. 10A-2), 15(FOG/ 10A-3), 20(FIG. 10A-4), 30(FIG. 10A-5), and 40(FIG. 10A-6) cycles of SPADT. The positive controls (top row of the multiarray) consisted of 0.01 nanogram of digoxigenin labeled DNA per spot.

FIG. 10B is a histogram depicting the quantitation of the results of the amplification of a DNA template in solution corresponding to the second row of the multiarray depicted in FIG. 10A. Quantitative analysis of the amplification products bound to nylon generated by specific primers are shown as follows: 4 pmol of 5' primer only (non-filled bars), 4 pmol of 3' primer only (lightly stippled bars), and 4 pmol of 5' and 3' primers (heavily stippled bars). The intensity of each spot was quantitated after magnifying the images and scanning the arrays using Adobe Photoshop and Image Quant Software as described elsewhere herein.

FIG. 11A, comprising FIGS. 11A-1 through 11A-6, is an image of a solid-phase multiarray depicting the amplification of DNA template bound to a nylon matrix, in the pattern depicted in FIG. 11A-1. Similarly to the experiment depicted in FIG. 10A, arrays of forward and reverse primers, either individually or as pairs, were spotted onto a nylon membrane at concentrations ranging from 4 pmol (second row from the top), 1 pmol (third row from the top), to about 0.5 pmol (fourth row from the top) and the primers were then UV-crosslinked (120 mJ/cm$^2$) to the Hybond Nylon. Ten nanograms of RGP DNA template were adsorbed to the nylon matrix, and the samples were examined after 10(FIG. 11A-2), 15(FIG. 11A-3), 20(FIG. 11A-4), 30(FIG. 11A-5) and 40(FIG. 11A-6) cycles of SPADT amplification. The positive controls (i.e., the top row of the multiarray) consisted of 0.01 ng of digoxigenin labeled DNA per spot.

FIG. 11B is a histogram depicting the quantitation of the results of amplification of a DNA template bound to nylon membrane corresponding to the second row from the top of the multiarray depicted in FIG. 11A. Quantitative analysis of the amplification products bound to nylon generated by specific primers are shown as follows: 4 pmol of 5' primer only (non-filled bars), 4 pmol of 3' primer only (lightly stippled bars), and 4 pmol of 5' and 3' primers (heavily stippled bars). The intensity of each spot was quantitated after magnifying the images and scanning the arrays using Adobe Photoshop and Image Quant Software as described elsewhere herein.

FIG. 12, comprising FIGS. 12A to 12D-4, is an image of a solid-phase multiarray depicting the effects on SPADT of the addition of excess human genomic DNA to a sample comprising plasmid target DNA (i.e., RGP+Human) compared with a sample of purified plasmid template without the addition of excess human genomic DNA (i.e., RGP) in the pattern depicted in FIG. 12A. Purified plasmid DNA at a concentrations ranging from 1 ng to 10 pg was used as the template in a SPADT reaction. In parallel experiments, the same concentrations of plasmid DNA were mixed with human DNA ranging in concentration from 100 ng to 500 ng. FIGS. 12B-1 to 12B-4 depict results obtained using 1000 (FIG. 12B-1), 50 (FIG. 12B-3), and 10 pg (FIG. 12B-4) of RGP DNA template. FIGS. 12-1 to 12C-4 depict results obtained using 1 ng RGP DNA template and 0 (FIG. 12C-1), 500 (FIG. 12C-2), 250 (FIG. 12C-3), and 100 ng (FIG. 12C-4) of human DNA template. FIGS. 12D-1 to 12D-4 depict results obtained using 100 ng human DNA template and 1000 (FIG. 12D-1), 100 (FIG. 12D-2), 50 (FIG. 12D-3), and 10 pg (FIG. 12D-4) of RGP DNA template.

FIG. 13, comprising FIGS. 13A to 13C-2, is an image of a solid-phase multiarray depicting the specificity of target amplification by SPADT. A multiarray containing duplicate matching forward and reverse primer pairs at 4pmol/spot (in the pattern depicted in FIG. 13A) were used to amplify adsorbed template DNA containing either HHV6 p41 (FIGS. 13B-1 and 13B-2) or RGP genes (FIGS. 13C-1 and 13C-2). After color development (CD); FIGS. 13B-1 and 13C-1. and scanning of the image, the amplification products were subjected to hybridization (H); FIGS. 13B-2 and 13C-2 with $^{32}$P-labeled probes specific for the target genes as described elsewhere herein.

FIG. 14A, comprising FIGS. 14A, 14A-1, and 14A-2, is an image depicting a multiarray demonstrating the use of reverse transcribed cDNA (RT-cDNA) and total RNA as template in a SPADT reaction. Total RNA was extracted from rabies virus (ERA strain) infected neonatal mouse brain seven days post-infection. The total RNA was reverse transcribed using oligo p(dT)$_{15}$ primers and approximately 0.5 μl of the total RNA sample was adsorbed onto a nylon membrane, in the pattern depicted in FIG. 14A. SPADT was performed using both specific (Rab 122/601) forward and reverse primer pairs and non-specific (HHV8 and HHV6 p41) forward and reverse primer pairs. Amplification product was detected only in spots comprising rabies-specific primer pairs.

FIG. 14A-2 is an image depicting a multiarray demonstrating the use of total RNA as template in a SPADT reaction. Approximately 0.5 μl of the total RNA sample was adsorbed onto nylon membrane, in the pattern depicted in FIG. 14A, and SPADT was performed using both specific (Rab 122/601) forward and reverse primer pairs and non-specific (HHV8 and HHV6 p41) forward and reverse primer pairs. No amplification product was detected using either specific or non-specific primer pairs.

DETAILED DESCRIPTION OF THE INVENTION

Figure 4B:
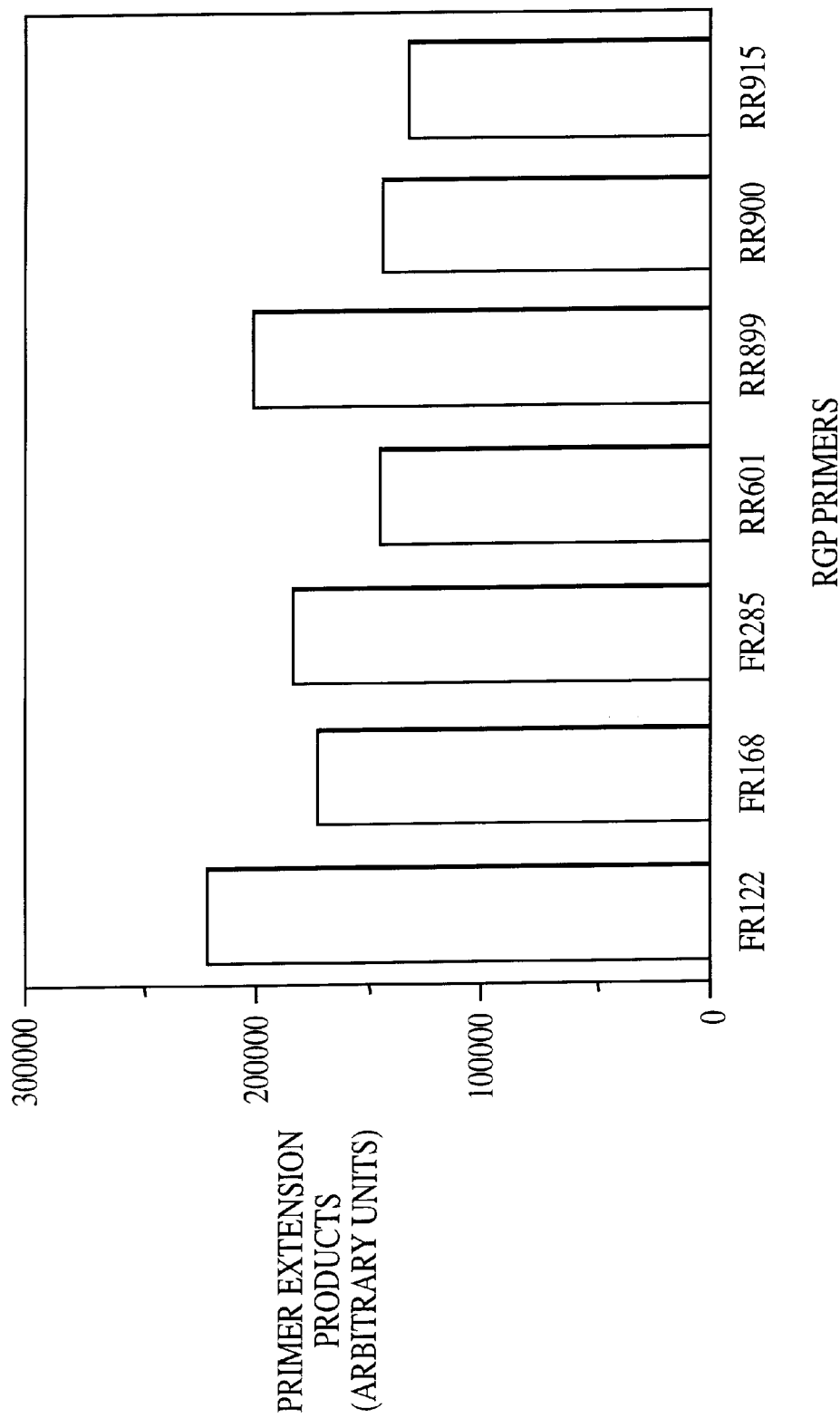

The invention is based on the discovery that solid-phase amplification of template DNA, where both reverse and forward primers are bound to a solid support and where the DNA template is also bound to the solid support, allows the rapid and efficient detection of specific target nucleic acid sequences using a multiarray method to process contemporaneously large numbers of samples. Binding of both forward and reverse primers to solid phase enables the amplification of the target nucleic acid sequence, thereby enabling the detection of single copy genes present in complex genomes. Binding of the DNA template increases the efficiency of the process and reduces the amount of time needed for such detection.

The present invention includes a method to detect the presence or absence of specific nucleic acid sequences in a biological sample. The method comprises performing an amplification reaction where a 5' and a 3' primer are irreversibly bound to a solid support and where the DNA is reversibly bound to the support.

One skilled in the art would appreciate, based on the disclosure provided herein, that the nucleic acid sequence being detected should be sufficiently unique to the organism such that the identical sequence with 100% homology at all primers used does not occur in another unrelated portion of the genome of the organism being examined. By using a sufficiently unique nucleic acid target sequence, any amplification product produced during the amplification phase will not be complementary to and, therefore, will not cross-hybridize and/or amplify the nucleic acids of other organisms under high stringency conditions.

Complementary refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

Homologous refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC3' and 5'TATGCG3' share 50% homology.

As used herein, "homology" is used synonymously with "identity."

Percent identity of one polynucleotide or polypeptide with respect to another polynucleotide or polypeptide may be determined using any available algorithm, such as the BLAST program.

A first oligonucleotide anneals with a second oligonucleotide with high stringency if the two oligonucleotides anneal under conditions whereby only oligonucleotides which are at least about 70%, and preferably at least about 90% or, more preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, for example, Sambrook et al., 1989, Molecular Cloning: A Laboratory Manual, Cold Spring Harbor Laboratory, New York, and Ausubel et al., 1997, Current Protocols in Molecular Biology, John Wiley & Sons, New York).

In one embodiment, in an amplification reaction used in the present method, a target nucleic acid unique to a specific gene is amplified by annealing two oligonucleotide primers, each being complementary to one of the two strands of the target, single stranded DNA. The primers which are irreversibly bound to a solid support, hybridize with their complementary strands on the target DNA and extension products are synthesized using DNA polymerase, at least four deoxyribonucleotide triphosphates (dNTPs), wherein at least one dNTP comprises a detectable label. The label is incorporated into the newly synthesized DNA during extension and amplification, thereby allowing the direct detection of the amplified product. The template target DNA and the extension products are separated from their complementary strands by denaturation at an elevated temperature, typically ranging from about 90° C. to about 100° C. although the method of the invention should not be construed to be limited to these temperatures. The reaction mixture is repeatedly cycled between a low temperature annealing step, usually ranging from about 50° C. to about 70° C., during which the primers hybridize to their complementary strands, an intermediate temperature (from about 70° C. to about 80° C.) primer extension step during which the primer copies the target template DNA, to the higher temperature denaturation step at a temperature from about 80° C. to about 100° C. These temperature steps, or thermal cycling, are repeated many times, typically about 20 to about 40 cycles are carried out, followed by a final synthesis step at about 70° C. and a 4° C. soak to stop the reaction.

Amplification reagents are the chemicals, apart from the target nucleic acid sequence, needed to perform the amplification process. As disclosed by Mayrand (1997, U.S. Pat. No. 5,691,146, which is incorporated by reference herein as if set forth in its entirety), these chemicals generally consist of five classes of components: (i) an aqueous buffer, (ii) a water soluble magnesium salt, (iii) at least four deoxyribonucleotide triphosphates (dNTPs) (conventionally, DATP, dTTP, dGTP, dCTP), (iv) oligonucleotide primers (typically two primers for each target sequence, the sequences defining the 5' ends of the two complementary strands of the double-stranded target sequence), and (v) a polynucleotide polymerase, preferably a DNA polymerase, more preferably a thermostable DNA polymerase, i.e., a DNA polymerase which can tolerate temperatures between 90° C. and 100° C. for a total time of at least 10 minutes without losing more than about half its activity.

Primers for the amplification steps could be the same if used for a reverse transcription step at the outset to convert RNA into DNA before carrying out the amplification procedure. However, in order to convert all the RNA into DNA, random primers are more desirable. Preferably, primers are chosen which only amplify target nucleic acid sequences of a gene of interest. In the examples in the present invention, the primers amplified only a target nucleic acid sequence within the selected gene, because they (the primers) have less than 60% sequence similarity to other sequences present in the remainder of the DNA being analyzed. Therefore, amplification using the preferred primers does not amplify other non-specific sequences, and thus will not give rise to detectable amplification products using the procedures disclosed in the present invention.

Preferred primer pairs and probes targeting various human and viral genes are shown in Table 1 and Table 2. However, the invention should not be construed to be limited solely to these sequences, but rather should be construed to encompass any and all useful primer pairs which may be identified as being useful following a reading of the present invention.

The oligonucleotide primers and probes of the invention may be conveniently synthesized on an automated DNA synthesizer such as a Perkin-Elmer (Foster City, Calif.) Model 392 or 394 DNA/RNA synthesizer using standard chemistries, such as phosphoramidite chemistry described in Beaucage and Iyer (1992, Tetrahedron 48:2223–2311), Molko et al. (U.S. Pat. No. 4,980,460), Koster et al. (U.S. Pat. No. 4,725,677), Caruthers et al. (U.S. Pat. Nos. 4,415,732 and 4,458,066). However, other similar syntheses using available chemistries and techniques may be used. Alternative chemistries resulting in non-natural backbone groups, such as phosphorothioate, phosphoramidate, and the like, may also be used provided the hybridization efficiencies of the resulting oligonucleotides are not adversely affected.

Oligonucleotide probes may be used to identify the amplification products following the amplification assay. Preferably, the oligonucleotide probe used to confirm the identity of the amplification product is in the range of about 15 to about 150 nucleotides in length. The precise sequence and length of an oligonucleotide probe of the invention depends in part on the nature of the target nucleic acid sequence to which it hybridizes. The binding location and length may be varied to achieve appropriate annealing and melting properties for a particular embodiment by one skilled in the art in accordance with known techniques.

The present invention includes primers of about 20 nucleotides in length. Preferably, the primers used to detect the nucleic acid sequence in a biological sample about 20 nucleotides or greater in size.

Oligonucleotides (both primers and probes) of the present invention include linear oligomers of natural or modified monomers or linkages, such as deoxyribonucleotides, ribonucleotides, and the like, which are capable of specifically binding to a target polynucleotide by way of a regular pattern of monomer-to-monomer interactions, such as Watson-Crick base pairing. Usually, monomers are linked by phosphodiester bonds or their analogs to form oligonucleotides ranging in size from a few monomeric units, e.g., 3–4, to several tens of monomeric units. Whenever an oligonucleotide is represented by a sequence of letters, such as "ATGCCTG," it will be understood that the nucleotides are in a 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphoranilidate, phosphoramidate, and similar compounds.

In another example presented herein, primers specific for rabies virus glycoprotein (RGP) were irreversibly bound to a nylon membrane. Template DNA comprising RGP DNA or non RGP DNA was amplified in solution using the bound primers. The amplification reaction was specific in that amplification products were produced only when DNA complementary to RGP was present in the PCR reaction. That is, no amplification products were produced where irrelevant primers such as E6 protein of human papilloma virus and human BCR and ABL gene primers were bound to the nylon and pSG5 plasmid DNA was used as the template DNA.

In additional examples, the above-described experiment was conducted in a similar manner to that just described, except that the DNA template was also bound, albeit reversibly, to the nylon membrane. In that instance, the primers were found to be specific for RGP and in addition, less DNA template was required in order to generate a detectable product. Therefore, although the invention encompasses an amplification reaction wherein the primers are bound to a solid support and the DNA template is in solution, the data disclosed herein demonstrate that amplification of DNA template when the template is also bound to the solid support is even more efficient than when the DNA template is not so bound. Thus, the present invention should be construed to encompass amplification of DNA where the primers are bound to a solid support and where the DNA template is in solution and/or where the DNA template is bound to the solid support as well.

As used herein, the term "DNA template" is the DNA to be amplified in the amplification reaction. This term is used herein to include the term "target nucleic acid."

By "irreversibly bound," as the term is used herein, is meant that the primers are attached to a solid support by a chemical, or other means, such that they remain bound to the support after washing of the support. One skilled in the art would appreciate based upon the present disclosure, that the manner by which the primers are bound to the solid support depends on, among other things, the type of solid support used.

By "solid support" as the term is used herein, is meant any matrix which is substantially solid and to which nucleic acid may be reversibly bound in the absence of any additional chemical or physical reaction. However, DNA may be irreversibly bound to the solid support useful in the present invention using a chemical or physical reaction to so bind the DNA. In one embodiment, the solid support is nylon membrane. However, the invention should not be construed to be limited to nylon membrane. Instead, the invention encompasses use of various solid supports such as, for example, nitrocellulose, and all those supports that are known to be able not only to bind the primers irreversibly but also to be able to bind the template DNA reversibly.

One skilled in the art will therefore appreciate, based upon the disclosure provided herein, that the method by which a primer is irreversibly bound to the solid support will depend, at least in part, on the type of solid support being used. Thus, in one embodiment, the solid support is nylon membrane and the primers are irreversibly attached via a string of contiguous T nucleotides (about 20 T nucleotides) at the 5' end of the primers. This string of T nucleotides facilitate the UV-crosslinking of the primers to the support. However, the present invention should not be construed to be limited use of poly-T stretches in the primers or to UV-crosslinking to irreversibly bind the primers to the solid support. Rather, the present invention includes, but is not limited to, irreversibly binding primers to any solid support by any method, chemical or otherwise.

The method of the invention further includes that the template DNA is reversibly bound to the solid support. In one embodiment, the DNA is adsorbed onto the solid support by simply spotting the DNA in aqueous buffer onto the nylon support. In another embodiment, the DNA is suspended in water and the solution is applied to the solid support, the wet solid support is sandwiched between coverslips, and the combination is then placed in the amplification reaction solution. However, the present invention should not be limited to suspending the DNA in water or to require that the solid support be sandwiched between coverslips. Rather, any method of applying DNA to a solid support as defined herein, which results in the DNA being reversibly bound to the support is included in the invention.

By the term "reversibly bound," as the term is used herein, is meant that the DNA template may be progressively released during thermocycling and/or it may be substantially removed from the solid support by standard washing methods. In one embodiment, the DNA may remain bound to the solid support, but can be progressively released during thermocycling such that, after 40 cycles, approximately 50% of the DNA is released. However, the present invention should not be construed to be limited to any particular percentage of the DNA being bound to the solid support. Rather, the present invention encompasses that from about 20% to about 80% of the DNA remains bound to the solid support after about 40 thermocycles.

In a preferred embodiment, the portion of the primers which is homologous to the template DNA is about 19 to about 23 nucleotides in length and is covalently linked to the 3' end of the poly-T stretch of each primer. However, the present invention should not be construed to be limited to any particular length of DNA homologous to the template DNA. Rather, the portion of the primers which is specific for the template DNA may range in length from about 15 nucleotides to about 100 nucleotides in length.

In one embodiment of the method of the invention, the primers and the template nucleic acid are incubated under "amplification conditions." By the term "amplification conditions," as that term is used herein, is meant any conditions under which DNA may be amplified. For example, as described elsewhere herein, the concentration of Taq polymerase and the addition of Triton X-100 detergent are several conditions which affect the efficiency of DNA amplification. The present invention should not be construed to be limited to any particular amplification conditions. Rather, the present invention includes conditions such as those described herein in the examples section, conditions that are well-known in the art, and the like.

By "amplification," as that term is used herein, is meant the synthesis of at least one nucleic acid strand which is complementary to the template strand. The kinetics of the amplification reaction may be, but are not limited to, linear, superlinear, and/or exponential kinetics.

In another embodiment of the method of the invention, the melting temperature between a primer and its complementary sequence in the DNA template ranges from about 55° C. to about 70° C. One skilled in the art would appreciate, based upon the disclosure provided herein, that the nucleic acid sequence of the primer may be designed so that the appropriate melting point is achieved using standard methods well-known in the art.

In another embodiment, the method of the invention includes that the primers be substantially lacking any GC rich regions near the 3' end of the primer. By "GC rich region," as the term is used herein, is meant any stretch of at least 4 to 5 guanidine or cytosine residues in a row.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an MRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A GC rich region is "near" the 3' end of the primer if the 3'-most G or C residue is within about 15 to about 7 nucleotides, more preferably from about 13 to about 8 nucleotides and even more preferably between about 12 nucleotides to within about 10 nucleotides from the 3' end of the primer molecule.

The method also includes that the amplification conditions include $MgCl_2$ at a preferable concentration of about 2 mM and KCl at a preferable concentration of about 50 mM.

In a preferred embodiment, the amplification reaction is a polymerase chain reaction. However, the present invention should not be construed as being limited to PCR amplification. Instead, the present invention includes, but is not limited to, the ligase chain reaction (Rouwendal et al., 1993, Biotechniques 15:68–76), and other such methods of nucleic acid amplification.

Detection of amplified nucleic acid is accomplished by detection of a label incorporated into the amplification product produced. In one embodiment, the label may be digoxigenin which may be detected immunologically. However, the present invention should not be construed to be limited to any particular method of detection of nucleic acids. Rather, a variety of art-recognized methods for detecting amplified nucleic acid are included in the present invention such as, but not limited to, incorporation of biotinylated nucleotides, radioactively labeled nucleotides, and the like.

In one embodiment, the template DNA to be detected includes RGP and HHV6p41. However, the present invention should not be construed to be limited to detecting any particular nucleic acid. Rather, the invention includes the detection of an infinite variety of nucleic acids of interest, including bacterial, viral, parasitic DNA, and other eukaryotic DNA, DNA comprising one or more mutations, genetically rearranged cancer genes, and genes associated with other diseases.

Further, one skilled in the art would appreciate, based on the disclosure provided herein, that the present invention is not limited to the detection of DNA in a sample. Rather, the starting nucleic acid may be RNA. Thus, the present invention encompasses the reverse transcription of RNA into DNA which may then be used in the method of the invention thereby detecting whether a particular nucleic acid is expressed in a sample.

Solid-phase amplification of DNA template (SPADT) provides the possibility of examining a DNA sample for the presence of a variety of genes. This methodology presents an alternative over the presently available multiarrays that are used for hybridization and detection of genetic material. The fact that the template amplification is carried out directly on the multiarray eliminates the need of the multiple steps necessary for separate template amplification and hybridization to confirm the identity of the amplification products.

Applications using SPADT include scanning of large genomic fragments for the presence of genes or gene families. Practical applications using SPADT can be envisioned in various areas such as the area of bacterial diagnostics by examining the ribosomal RNA genes, the area of viral diagnostics by scanning for the presence of viral nucleic acid sequences (members of the herpesviruses, adenoviruses, and other DNA and RNA virus families) in a sample, in the areas of forensic medicine using the detection and identification of species specific sequences or for the presence of, for example, specific major histocompatibility complex (MHC) genes. Finally, coupling of SPADT with a reverse transcriptase carried out in solution facilitates the analysis of expressed genes and viral RNA genes using the method of the invention.

The data disclosed herein demonstrate a low cost methodology based on solid-phase template amplification that can be utilized to detect low abundance genetic information in a complex nucleic acid sample using multiple amplification reactions. High throughput analysis of DNA using hybridization to microarrays of immobilized oligonucleotide probes is becoming increasingly utilized for polymorphism screening and genomic mapping (White et al., 1989, Trends Genet. 5:185–189). However, such analysis requires multiple steps including labeling the template, hybridization that defines which DNA sequences are present in the sample, and a read out step using appropriate instrumentation (Lockhart et al., 1996, Nature Biotechnology 14:1675–1680; Castellino, 1997, Genome Res. 7:943–946; Kricka, 1998, Nature Biotechnology 16:513–514; and Ramsay, 1998, Nature Biotechnology 16:40–44). The present invention discloses an alternative and more rapid method to interrogate a DNA sample. The method disclosed herein combines, in a single step, target DNA template amplification with the specificity of detection of amplified products thereby accelerating and simplifying the detection process.

The method utilizes multiarrays of highly specific forward and reverse specific primer pairs, UV-crosslinked to Hybond-N membranes. Further, the method includes adsorbed DNA templates which generate more abundant amplification products than DNA templates which are in solution. Solid phase amplification of template DNA in a multiarray setting as disclosed herein eliminates the need for multiple independent amplifications, e.g., a single sample may be examined for the presence of one or multiple members of a gene family. The amplified product may be labeled with a reporter molecule such as digoxigenin and the amplified target DNA can be visualized on the solid support as a discrete spot. This non-radioactive detection method, which is simple and inexpensive, has the further advantage of being readable with very inexpensive instrumentation (e.g., a computer scanner) and software (e.g., Adobe Photoshop). Alternatively, more efficient methods of detection, such as using a chemiluminescence step, can be easily adapted to the present invention.

The SPADT multiarray approach is valuable in particular diagnostic settings, including, for example, where there is a need to determine if viral sequences, genetic rearrangements, or specific alleles of a large family of genes are present in a particular sample. One challenge to developing such diagnostic multiarrays is the requirement of highly specific primers all of which can efficiently function at the same cycling conditions and at the same $Mg^{2+}$ and $K^+$ concentration. The data disclosed herein demonstrate a method for designing such specific primers for viral genes in which the specificity of the primers can be defined experimentally by comparing multiple primer extensions of the specific target sequences and of non specific DNA. Further, the data disclosed herein teach several features for designing such primers, and a detailed analysis providing an algorithm will be described elsewhere. For instance, these general features for the design of specific PCR primers suggest features for selecting primers with melting temperatures within a narrow range (i.e., 55° C.–59° C.) and with a 40–60% GC content. In sum, the data disclosed herein demonstrate the role of oligo dT tracts and of GC boxes in affecting specificity wherein such features play an important role in the design or primers that may be UV-crosslinked to a solid matrix and which provide high specificity of sequence recognition.

In SPADT, the specificity of the amplified products can be confirmed experimentally by hybridization of the products to specific probes after colorimetric detection of the amplified signal. Such a hybridization step is not desirable in a routine diagnostic set-up since it is time consuming and cumbersome. However, the need for a hybridization step can be circumvented using a multiarray setting by examining multiple target sequences for each gene under investigation and eliminating potential artifacts, thereby obviating the need to confirm the identity of each of the products by a hybridization step through the use of redundant confirmation. This approach is particularly advantageous for detection of foreign sequences, such as those of viruses and bacteria, in a complex sample.

The advantages of SPADT over conventional PCR are threefold: 1) SPADT abolishes the need to run hundreds of parallel reactions when detection of one of many possible target genes is being attempted, 2) by crosslinking both the forward and reverse primers to a solid support, it is possible to avoid the competition between different sets of primer pairs commonly observed in multiplex PCR, and 3) the DNA template being adsorbed to the solid-phase allows relatively high localized concentrations of DNA using small DNA samples. Thus, the present invention offers many advantages over prior art techniques. The data disclosed herein demonstrate the use of a nylon matrix rather than, for example, glass matrixes. The data further indicate that it is currently technically feasible to array on a nylon matrix 5 nl primer spots with less than 400 μm spacing between spots. Moreover, both sides of the nylon can be used thereby effectively doubling the number of potential questions that can be addressed to a small DNA sample. Further, the nylon matrix allows the use of primers that do not require expensive modifications. Therefore, the use of a nylon matrix, or other membrane matrix such as, e.g., nitrocellulose, disclosed in the present inventions offers several advantages although the invention should not be construed as being limited to any particular solid support.

In addition, the SPADT method disclosed herein differs from the "bridge" PCR technology (U.S. Pat. No. 5,641,658) in that, inter alia, not only the primer pairs but also the DNA template are bound to the solid substrate thereby markedly increasing the efficiency of the reaction. This efficiency cannot be achieved with a glass matrix. Reed and Mann (1985, Nuc. Acids. Res. 13:7207–7221) have reported that double stranded DNA can efficiently bind to Hybond-N nylon membranes; however, the results disclosed herein indicate that temperature cycling slowly releases the bound DNA. Also, unlike "bridge" PCR, SPADT uses unmodified primers, which are readily available commercially, and a very inexpensive solid-phase matrix. Most important from an economical point of view, the present invention encompasses a method of detection and quantitation that does not require highly expensive instrumentation (Editorial, 1998, Nature Genet. 18:195–197).

The data disclosed herein demonstrate superlinear amplification utilizing forward and reverse primer pairs in the presence of sufficient forward and reverse primer concentrations. Such superlinear amplification is sufficient for detection of a low concentration of template in the picogram range. Further, the SPADT provides the possibility of interrogating a DNA sample for the presence of a variety of genes and should present an alternative over the presently available multiarrays that use hybridization for detection of genetic material.

In sum, most of the prior art methods for detection of PCR amplified products are not suitable for mass screening since they involve steps such as electrophoresis, radioisotopes or centrifugations requiring extensive sample processing by a person trained in these techniques (White et al., 1989, Trends Genet. 5:185–189). Although methods of detection of different expressed gene sequences in the multiarray format in DNA chips are now available (Lockhart et al., 1996, Nat. Biotech. 14:1675–1680; Castellino, 1997, Genome Res. 7:943–946; Kricka, 1998, Nature Biotech. 16:513–514; Ramsay, 1998, Nature Biotech. 16:4044), cost effectiveness is a major concern when one must implement those available expensive methodologies in real life situations for the diagnostic perspective. The present invention provides an efficient, cost effective method to detect low abundance nucleic acid sequences in a complex sample. The invention further provides methods of interrogating a complex sample to detect the presence of myriad nucleic acid sequences of interest within a single complex sample, e.g., the sample may contain the sequence information for a large genome. For example, this method allows a sample of human blood to be examined to detect the presence of a variety of pathogens.

The invention further includes a method of designing a primer which amplifies a nucleic acid provided the nucleic acid is present in a sample comprising DNA. This method comprises the following steps. A) At least one 5' and one 3' primer homologous to the nucleic acid are synthesized. B) An amplification reaction is performed wherein a solid support on which the primer is irreversibly bound and the DNA is reversibly bound is incubated under amplification conditions to generate an amplified nucleic acid. C) The specificity of the primer is determined by comparing the ability of the primer to produce a detectable amount of the amplified nucleic acid in the amplification reaction in the presence or absence of the nucleic acid, wherein a detectable amount of amplified nucleic acid in the amplification reaction in the presence of the nucleic acid, compared with the absence of a detectable amount of the amplified nucleic acid in the absence of the nucleic acid, is an indication that the primer is specific for amplifying the nucleic acid. D) The characteristics of the primers of step (C) which are specific for the nucleic acid are compared with each other to identify common features shared among the most specific of the primers. E) Additional primers are synthesized incorporating the features identified in step (D), thereby designing a primer which amplifies a nucleic acid provided the nucleic acid is present in a sample comprising DNA.

In one embodiment of this method of the invention, the comparing step is performed using an algorithm which takes into account the information obtained in step (C).

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

SPADT and Detection of Single Copy Genes in Complex Genomes

The experiments presented in this example may be summarized as follows.

The data disclosed herein demonstrate the development of a simple solid-phase amplification of template DNA for efficiently and simultaneously scanning complex genomes for the presence of a large number of genes. This type of approach is valuable in particular situations, for example, to detect the presence of viral sequences, genetic alterations, and/or specific alleles of a large family of genes (e.g., MHC, globins) in a sample.

SPADT utilizes UV crosslinking of pairs of T tailed forward and reverse primers to a nylon matrix in microdots of less than 500 µm in diameter and at a concentration sufficient to generate a superlinear amplification of the template. Moreover, the data demonstrate that superlinear amplification occurs once a primer pair density of at least 1 attomol/µm$^2$ of solid phase surface is achieved. Sufficient sensitivity in detection of amplified sequences can be achieved using a non-radioactive methodology. For example, the amplified products labeled with digoxigenin can be easily detected immunologically. Additionally, the sequence identity of the amplification product can be formally demonstrated by in situ hybridization with a diagnostic DNA probe.

The data further disclose that, in order to provide specific amplification, it is important to qualify and run the primers prior to using them in the assay. Adequate specificity is provided by the use of a Taq polymerase buffer that reduces specific macromolecule interactions. Further, the specificity of amplification can be readily optimized in a multiarray by carrying out multiple independent amplifications of the same gene using different primer pairs and by the built-in presence of negative controls consisting of primers specific for a variety of non relevant genes. The amplified signal obtained on solid phase can be recorded after magnification using available image scanners and can be quantitated using available software, thus eliminating the need for more expensive complicated instrumentation and further simplifying the procedure.

The Materials and Methods used in the experiments presented in this example are now described.

Oligonucleotide Primers

Oligonucleotide primers with 5' thymidine (T) leader sequences were purchased from Integrated DNA Technologies (Coralville, Iowa) and were purified by polyacrylamide gel electrophoresis (PAGE). The sequences of all primers used in the experiments described herein are listed in Table 1 and Table 2.

An oligonucleotide primer containing 20 mer 5' T leader sequences and labeled at the 3' end with 3' Digoxigenin-VN CPG with a deoxyribose linking arm obtained from Clontech Laboratories, Inc. (Palo Alto, Calif.), was used as a positive control for the immunodetection step and as an internal standard in quantitation assays.

The initial design of the primers suitable for experiments was based on Oligoversion 4.0 Software program (National Biosciences, Inc., Plymouth, Minn.). The primers had a 5' T leader sequence of 20 mer followed by 25 mer coding sequence specific for the target nucleic acid sequence of interest. The coding sequence had a calculated melting point of at least 62° C. as estimated by the nearest neighbor method as described in, for example, Breslauer et al. (1986, Proc. Natl. Acad. Sci. U.S.A. 83:3746–3750).

DNA Templates

A pSG5 plasmid vector containing the RGP gene insert (1632 bp) of the rabies virus and yielding a recombinant construct having a total size of 5727 bp (Anilionis et al., 1981, Nature 294:275–278) was used in the initial experiments. The primary target sequence for PCR amplification was a segment of the RGP gene yielding an amplification product with a predicted length of 691 bp as specified by the primer pair.

Other target sequences on the RGP gene were of about 700 to about 800 bp. Human genomic DNA was extracted from a cell line (ALL 1) using the Acu Gen DNA extraction kit from Biotronics Technologies, Corp. (Lowell, Mass.). The amount of DNA present in was quantitated by determining the OD$_{260\,nm}$ using the spectrophotometer.

Solid Phase

The solid phase consisted of 48 mm$^2$ (4×12 mm) strips of Hybond-N (Amersham Pharmacia Biotech, Arlington Heights, Ill.), a neutrally charged nylon membrane. The membrane, which is both DNA/RNAse-free and chemically inert, was used without prior washing. The dimension of the solid phase membrane was optimized to fit in a microfuge tube containing a 200 µl volume of reaction mixture.

Multiarrays

Multiarrays were prepared using an Auto-Spot Robot ASP 222, (Abimed, Analysen Technik, Germany), consisting of a robotic arm equipped with a syringe, which is capable of depositing minute quantities of liquid. In certain experiments, a custom-made arrayer with the capability to spot even smaller volumes was used.

The volume spotted for different experiments ranged from 5 nl to 200 nl per spot. Either one primer or a pair of primers (forward and reverse) at concentrations ranging from 2 fmol to 10 pmol were spotted. Two hundred nl of primers in solution generated spots of less than 500 µm in diameter using this system.

In order to monitor the quality of the spots in the multiarrays, the oligonucleotide primers were diluted in water containing phenol red (0.0015%), and the indicator dye generated a yellow spot when the primers were arrayed on nylon. The phenol red dye was rapidly washed away without interference during PCR and did not interfere with PCR or with the subsequent color development of the amplified product. Spacing between spots ranged from 2.5 mm to 1.0 mm depending on the experiments. The primers spotted onto the membrane were bound entirely to the nylon surface and both sides of a nylon strip could be spotted making it possible to utilize multiarrays of primers on both sides of the membrane.

UV Crosslinking of Primers onto Solid Phase

Figures 1, 2, 3, 4, 5, 6, 11A:
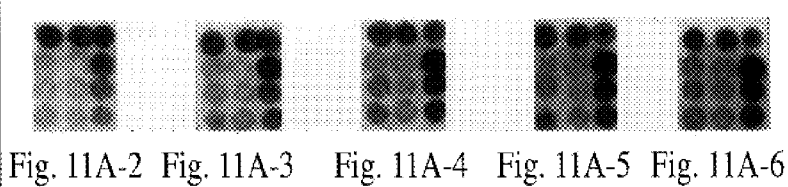

Forward and reverse oligonucleotide primers specific for a target RGP gene were spotted onto the nylon membrane and the membrane was dried at room temperature for 30 minutes and then the nucleic acids were crosslinked to the membrane using a UV Stratalinker 1800 (Stratagene, La Jolla, Calif.) at exposure levels from about 0 to about 240 mJ/cm$^2$. The data disclosed herein indicate that while lack of UV-crosslinking caused a poor amplification, a progressive amplification was observed with proper crosslinking (FIG. 2).

The optimal conditions for UV crosslinking of the primers to Hybond-N and the optimal concentration of primer pairs to be bound for efficient solid-phase PCR was determined by spotting progressively increasing concentrations of primer pairs then crosslinking, by increasing exposure to UV light. The data disclosed herein demonstrate that a length of the 5' T leader sequence of from about 15 to about 30 nucleotides 5' upstream of a 20 mer sequence specific primer was adequate for UV crosslinking of oligoprimers to Hybond N providing sufficient stability during PCR thermal cycling conditions during for 40 cycles (FIG. 1). Therefore, in all the experiments described herein, oligonucleotide primers that had a 20 mer T-leader sequence followed by a 20 mer specific primer were used.

Polymerase Chain Reaction

PCR was carried out using a PTC-100 Thermocycler (MJ-Research, Inc., Watertown, Mass.) in a microfuge tube containing 200 µl of reaction mixture and using from about 2 to about 4 µl of Platinum Taq™ DNA Polymerase (GIBCO/BRL, Gaithersburg, Md.) with magnesium supplied separately from the aqueous buffer. All other reagents used were at standard PCR concentrations, as prescribed by GIBCO/BRL. The PCR mixture was supplemented with Triton X-100 at a final concentration of from about 0.5 to about 2.5% and with dimethyl sulfoxide (DMSO) at a final concentration ranging from about 1 to about 15%. Digoxigenin-11-2'-deoxy-uridine-5'-triphosphate (alkali-stable dUTP; Boehringer Mannheim, Indianapolis, Ind.) was added to the PCR mixture at a final concentration of about 60 nM while the amount of unlabeled dTTP was kept constant at the standard 200 µM concentration.

The PCR thermal cycling conditions were as follows: denaturation at 95° C. (1 minute), annealing at 55° C. (2 minutes), extension at 72° C. (2 minutes). Thermal cycling at these three times and temperatures was repeated 40 times and was followed by an extension step at 72° C. for 10 minutes. The data disclosed herein suggested that Hybond N interfered with Taq polymerase activity both when the PCR was carried out in solution and when it was carried out in solid phase. This reduction in Taq polymerase activity was not relieved by prewashing the Hybond-N membrane with detergents or salt solutions thereby ruling out possible contaminants in the nylon filter. However, the solution PCR in the presence of Hybond-N could be restored to the same efficiency of a PCR in solution carried out in the absence of the Hybond-N by either increasing the concentration of the Taq polymerase in the reaction mixture or by adding Triton X-100 to the reaction mixture (FIGS. 6 and 7). Similarly, the efficiency of PCR in solid phase was also increased by these two adjustments to the procedure. Accordingly, both a high Taq polymerase concentration of 1 µl of Taq polymerase per 100 µl of PCR mixture and 1% Triton X-100 were used in the experiments described herein.

Detection of the Synthesized PCR Products

The dUPT-igoxigenin-labeled-PCR amplification products were detected using the Genius 3 System Nonradioactive Nucleic Acid Detection Kit (Boehringer Mannheim, Indianapolis, Ind.), which detects digoxigenin-labeled nucleic acids by immunoassay using an enzyme-catalyzed color reaction. The calorimetric detection method was performed per the manufacturer's instructions, with the exception that the reaction volumes were decreased to 1 ml per step. The optimal time length for the color development step, wherein the membranes were exposed to the digoxigenin color substrate NBT/BCIP solution, was found to be 20 minutes.

Scanning and Quantitative Analysis of the Multiarrays

The nylon strips were scanned at a resolution of 1200 dpi using an Astra 610 S 30 bit color scanner (Umax Technology, Inc., Fremont, Calif.) and Vista Scan 2.4 (Fremont, Calif.) and Adobe Photoshop 4.0 Software (Adobe Systems, Inc., San Jose, Calif.). The magnified scanned images were converted into a grayscale mode and saved as tag image file format (TIFF) inverted files. The TIFF inverted files were used for quantitation of the intensity of the signal in each spot by Image Quant 1.2 Software using the user volume method (Molecular Dynamics, Sunnyvale, Calif.).

Hybridization of Multiarrays with Radiolabeled Probes

In some experiments, selected nylon strips containing PCR amplified multiarrays which had been scanned as described previously herein, were subjected to hybridization at 52° C. with probes specific for the amplified target nucleic acid segment. Briefly, probes were labeled with $^{32}$p using the method of Yamada et al. (1989, Proc. Natl. Acad. Sci. U.S.A. 86:5123–5127) and hybridized to the nylon strips at 50° C. The filters were washed with 6×SSC at 2° C. below the calculated melting point and exposed to X-ray film at −70° C. overnight.

The Results of the experiments presented in this example are now described.

Establishing Optimal Conditions for SPADT

The optimal conditions for UV crosslinking of the primers to Hybond-N and the optimal concentration of primer pairs to be bound for efficient solid-phase PCR were determined by spotting progressively increasing concentrations of primer pairs then crosslinking, by increasing exposure to UV light. The data disclosed herein demonstrate that a length of the 5' T leader sequence of from about 15 to about 30 nucleotides 5' upstream of a 20 mer sequence specific primer was adequate for UV crosslinking of oligoprimers to Hybond N providing sufficient stability during PCR thermal cycling conditions during for 40 cycles (FIG. 1). Further, the data disclosed establish that primers without a poly-dT leader sequence were released from the nylon matrix during cycling (FIG. 1). Primers containing a poly dT leader sequence of 15 or or 20 mer remained bound to the matrix to a similar extent as primers containing a poly dT leader sequence of 50 and 80 mer in length. Therefore, in all the experiments described herein, oligonucleotide primers that had a 20 mer T-leader sequence followed by a 20 mer specific primer were used.

The optimal UV dose for crosslinking the poly dT-containing primers to a nylon matrix was also determined. The data disclosed herein (FIG. 2) demonstrate that, using forward and reverse primers comprising a 20 mer poly dT leader sequence and a 20 mer coding sequence homologous for the RGP gene spotted on the membrane in concentrations ranging from 2 fmol to about 4 pmol, the efficiency of the primers to generate amplification products was dependent upon the UV dosage used to crosslink the primers to a nylon membrane which dosage ranged from 0 to about 200 mJ/cm$^2$. More specifically, the data disclosed herein indicate that lack of UV irradiation resulted in loss of the ability of the primers to amplify the DNA template. However, a UV dose ranging from about 40 to about 120 mJ/cm$^2$ was sufficient to generate a detectable amplification product.

Having established the optimal poly dT leader sequence length (i.e., 20 mer) and the optimal UV crosslinking dosage (i.e., about 120 mJ/cm$^2$), the optimal concentration of primers to be bound to nylon membrane was also determined (FIG. 3). Briefly, increasing amounts of primers specific for RGP ranging from 2 fmol to about 4 pmol were spotted onto nylon. The data disclosed herein demonstrate that increasing the concentration of the primers up to 4 pmol per spot increases the intensity of the signal. Further, the results indicate that at from about 2 pmol to about 4 pmol of primer concentration, the primer concentrations appear to be providing an optimal level of amplification efficiency.

Additionally, the data disclosed herein demonstrate that increasing the concentration of Taq polymerase increased the efficiency of amplification of DNA template bound to solid phase (FIG. 6). Moreover, adding fresh Taq polymerase to the SPADT reaction after twenty-five PCR cycles further increased the efficiency of amplification (FIG. 8).

The data disclosed herein suggested that the nylon membrane interfered with Taq polymerase activity both when the PCR was carried out in solution and when it was carried out in solid phase. Prewashing the nylon did not reduce the interference of the membrane with Taq polymerase activity nor was it decreased by prewashing the Hybond-N membrane with detergents or salt solutions thereby ruling out possible contaminants in the nylon filter as a source of Taq polymerase inhibition. However, the addition of Triton X-100 detergent to the PCR reaction mixture restored Taq polymerase activity to the same efficiency of Taq polymerase in a PCR in solution carried out in the absence of the Hybond-N (FIG. 7). Increasing the concentration of the Taq polymerase in the reaction mixture also diminished the inhibitory effect(s) of the nylon membrane on Taq polymerase. (FIG. 6). The efficiency of PCR with the DNA template bound to solid phase was also increased by these two adjustments to the procedure. Both high Taq polymerase concentration or 1% Triton X-100 coupled with a concentration of 1 μl of Taq polymerase per 100 μl of PCR mixture were used in the experiments described herein.

Detection of Target DNA by SPADT

Forward and reverse primers specific for the RGP gene were arrayed on Hybond-N strips either individually or as primer pairs along with irrelevant primers (i.e., primers specific for the sequence encoding the E6 protein of human papilloma virus and for sequences encoding the human proteins BCR and ABL (Mar-Aguilar et al., 1998, Clin. Lab. Haematology 20:221–224 as shown in Table 1) at a final concentration of 0.5 pmol/spot. A solid phase-PCR was carried out for 40 cycles with a reaction mixture containing the pSG5 plasmid DNA template (20 ng), Taq polymerase (ranging in concentration from about 1 μl to about 4 μl/100 μl of reaction mixture), nucleotide triphosphates (dNTPs), and digoxigenin-labeled-dUTP, all in the absence of Triton X-100 detergent.

TABLE 1

| Target Code | SEQ ID NO: | Primer Sequence | Tm | GC (%) |
|---|---|---|---|---|
| RGP FR164 | 1 | 5'(20T)A TTT GGT AGT GGA GGA CGA AGGA-3' | 68.4 | C.48 |
| RGP FR165 | 2 | 5'(20T)TTT GGT AGT GGA GGA CGA AG-3' | 61.9° | C.50 |
| RGP FR122 | 3 | 5'(20T)C CTG GAG GCC GAT TGA CAT AC-3' | 68.4° | C.57 |
| RGP FR285 | 4 | 5'(20T)G GCT GAA ACC TAC ACT AAC T-3' | 55.5° | C.45 |
| RGP FR168 | 5 | 5'(20T)G GTA GTG GAG GAC GAA GGA T-3' | 62.2° | C.55 |
| RGP FR273 | 6 | 5'(20T)G GTT GTG ACG GAG GCT GAA A-3' | 68.6° | C.55 |
| RGP FR336 | 7 | 5'(20T)A AAG CAT TTC CGC CCA ACA C-3' | 69° C. | 50 |
| RGP FR170 | 8 | 5'(20T) T AGT GGA GGA CGA AGG ATG C-3' | 64.2° | C.55 |
| RGP FR166 | 9 | 5'(20T)T TGG TAG TGG AGG ACG AAG G-3' | 64.2° | C.55 |
| RGPRR855 | 10 | 5'(20T)C AAC TGA TCG GGA GGG CAC CAT T-3' | 75.5° | C.57 |
| RGPRR899 | 11 | 5'(20T)A CAA GGT GCT CAA TTT CGT C-3' | 61.8° | C.45 |
| RGPRR797 | 12 | 5'(20T)C CAT CCA TAA GTC TAA GTC C-3' | 55.4° | C.45 |
| RGPRR601 | 13 | 5'(20T)G GTT AGT GGA GCA GTA GGT AGA-3' | 60.1° | C.50 |
| RGPRR900 | 14 | 5'(20T)A ACA AGG TGC TCA ATT TCG T-3' | 61.6° | C.40 |
| RGPRR915 | 15 | 5'(20T)G ACC AAC TCC TCT ACA ACA A-3' | 56.3° | C.45 |
| RGPRR713 | 16 | 5'(20T)A CAA AGC CGC AAG TCT CAC T-3' | 64.1° | C.50 |
| RGPRR715 | 17 | 5'(20T)C TAC AAA GCC GCA AGT CTC A-3' | 63.1° | C.50 |
| RGPRR719 | 18 | 5'(20T)T CAT CTA CAA CGC AGC AAG T-3' | 62.7° | C.45 |
| RGPRR720 | 19 | 5'(20T)T TCA TCT ACA AAG CCG CAAG-3' | 63.4° | C.45 |

As demonstrated in FIGS. 4A and 4B, the cDNA synthesized in solid phase is primer-dependent and primer-specific and the amount of the product is proportional to the concentration of Taq polymerase used in the reaction (FIGS. 4A and 6). Quantitative analysis of the same experiment also demonstrates that the intensity of staining of the synthesized product during SPADT when both forward and reverse primers are used is higher than the intensity of staining of the array when the forward and reverse primers are used separately (FIG. 4B).

SPADT is Linear or Superlinear Depending on Various Reaction Parameters

In order to more accurately define whether the accumulation of the newly synthesized DNA strands in SPADT was linear (i.e., the result of repeated primer extensions) or superlinear (i.e., due to the contribution of an increasing concentration of template available at every new cycle), the following experiment was conducted. Nylon filters were spotted with 200 nl of individual primers and with primer pairs at final concentrations ranging from about 20 fmol to about 4 pmol/spot. The arrays were subjected to SPADT in the presence of 20 ng of the pSG5 plasmid DNA containing the RGP gene target insert using 4 $\mu$l/100 $\mu$l of Taq polymerase. The amplification products were detected as digoxigenin-positive spots after 10, 15, 20, 30 and 40 cycles (FIG. 10A). The results indicated that the accumulation of an amplified product in the presence of single primers was linear but the presence of primer pairs generated a superlinear amplification reaching saturation as a function of both the primer concentration and the number of cycles.

The quantitation experiment was repeated using multiarrays containing spots generated with smaller volumes (from 5 to 100 nl) (FIG. 10B). The quantitation results of 4 representative experiments are shown in Table 2 and indicate that the solid phase PCR was linear when the concentration of the primer pairs was at or below 200 fmol/spot/primer, but the solid phase PCR became progressively superlinear when the concentration of the primers was increased to greater than 200 fmol/primer/spot.

Detection Limits of SPADT

In order to determine the minimum concentration of a target DNA template sufficient for detection using SPADT, decreasing concentrations of RGP-containing pSG5 plasmid were used as a template in a SPADT reaction. The results indicated that 10 pg of plasmid template were sufficient for detectable amplification of the RGP gene after 40 cycles of PCR (FIG. 12). The data disclosed herein indicate that excess human DNA interferes with the amplification of the purified plasmid. Further, concentrations of about 100 ng of genomic DNA do not interfere drastically with the sensitivity of DNA template detection; however, this sensitivity of detection is decreased particularly at levels below 10 pg of plasmid DNA template.

The reaction was further optimized by taking the following steps: increasing the concentration of primers pair/spot to range from about 5 to about 10 pmol/spot; adding fresh Taq polymerase after 25 cycles (FIG. 8); and extending the reaction to 50 cycles. The results indicate that under these conditions, about 5 pg of input plasmid equivalent to as little as 1.5 pg of the target RGP sequence could be detected as an amplification product by the solid phase multiarray method of the instant invention (FIG. 9).

The data disclosed herein demonstrate that, despite prior art teachings to the contrary (see, e.g., Saiki et al., 1989, Proc. Natl. Acad. Sci. U.S.A. 86:6230–6234), relatively short T-tails at the 5' end of the oligonucleotide primers are sufficient to anchor the primers to nylon solid phase and withstand thermal cycling during SPADT. Although the work of Saiki et al., supra, teaches that long T-tailed oligonucleotide primers of up to 800 nucleotides have a higher retention rate on nylon filters upon UV crosslinking than oligonucleotides having shorter T tails, the additional complexity of enzymatic addition of a long homopolymeric tail renders prior art methods undesirable. Therefore, the method of the invention, by using 20 mer T-leads to UV crosslink the primers for solid phase-PCR, represents a significant improvement over prior art methods.

It is well known that exposure of oligonucleotides to UV leads to activation of thymidine that becomes able to covalently couple with the primary amine moiety present in nylon (Church and Gilbert, 1984, Proc. Natl. Acad. Sci. U.S.A. 81:1991–1995). Accordingly, since the crosslinking is favored by the presence of stretches of multiple Ts, it is important in the design of the oligonucleotides primers utilized in the multiarray solid-phase-PCR to avoid stretches of T in those regions of the oligonucleotide that are expected to remain free to hybridize to the target template.

Important factors which must be considered to carry out a SPADT reaction using a nylon solid phase are the need to avoid sequestration of the polymerase by the nylon filter and a sufficient (200 fmol or higher) concentration of primer pairs bound to the solid phase. Further, the superlinear amplification of the target template was found to occur at a minimum concentration of 200 fmol per each primer. This concentration translates to a concentration of approximately 1 attomol/$\mu^2$ for each primer and apparently allows sufficient interaction between the newly formed DNA strand and the complementary primers.

Additionally, the observation that Taq polymerase activity is decreased in the presence of nylon filters may be explained by the known ability of nylon filters to adsorb protein on their surfaces. This putative sequestration of protein by nylon can be efficiently avoided by using Triton X-100 in the reaction mixture as demonstrated herein (FIG. 7). Attempts to block the membrane surface with an excess of proteins (e.g., casein) yielded unreliable results.

EXAMPLE 2

SPADT Amplification of DNA Template using Multiarrays of Anchored Primer Pairs and Adsorbed DNA Template The experiments presented in this example may be summarized as follows.

The conditions for SPADT using an adsorbed DNA template and using forward and reverse primer pairs anchored to a solid-phase substrate were examined utilizing two target viral DNA sequences. Arrays of primers with a 20 mer oligo dT-leader sequence at their 5'-end followed by 19–23 mer specific coding sequence were UV crosslinked to a Hybond-Nylon membrane by UV radiation to provide a stable binding during thermocycling conditions. Specific and efficient primers suitable for solid-phase amplification of the target DNA template were identified by multiple cycles of primer extension in solid-phase. Superlinear amplification of the target DNA was achieved when matching pairs of forward and reverse primers were anchored at adequate density. Improved efficiency of priming was observed when the DNA template was also adsorbed to the solid-phase containing the arrayed primer pairs. SPADT provides the advantages of allowing high throughput multiarray scanning of uncharacterized DNA templates for the identification of underrepresented foreign sequences, like viruses, bacteria or fungi, or the identification of other unique genetic sequences like molecular DNA rearrangements present in a small fraction of the total DNA being sampled.

The Materials and Methods used in the experiments presented in this example are now described.

Oligonucleotide Primers

Oligonucleotide primers, designed using Oligoversion 4.0 software (National Biosciences, Inc., Plymouth, Minn.) containing an oligo-dT leader sequence at the 5' end followed by specific coding sequence, were purchased from Integrated DNA Technologies (Coralville, Iowa). The sequences of the primers used in the experiments disclosed herein are listed in Table 2.

In preliminary experiments, the minimum length of oligo-dT leader sequence required for stable binding of the primers (following Uw crosslinking) to the nylon matrix during at least for 40 cycles of temperature shifts ranging from 550 to 95° C. was determined. Briefly, forward and reverse primers containing oligo-dT leader sequences ranging from 80 mer to 0 mer were UV crosslinked to nylon filters. A template amplification reaction was carried out using a plasmid DNA in solution as the template. The presence of amplified products was monitored in the solid-phase and in the solution reactions. The results indicated that oligo-dT leader sequences as short as 15 mer were capable of withstanding multiple temperature cycles without detaching from the filter and were capable of generating an amplified product on solid-phase. Such conditions did not generate any detectable product in the solution reaction. Therefore, routinely, the primers used for the solid-phase amplification included an oligo-dT leader sequence of about 20 mer followed by a specific coding sequence of about 19–23 mer.

DNA Templates

A pSG5 plasmid vector containing the rabies virus glycoprotein (RGP) gene (1632 bp) and (Anilionis et al., 1981, Nature 294:275–278) was used in some experiments. The target DNA for amplification were sequences of the RGP gene ranging from 692 bp to 778 bp. In other experiments, the HHV6p41 gene (Agulnick et al., 1993, J. Gen. Virol. 74:1003–1009) subcloned in a Bluescript vector was used. The target p41 gene was approximately 800 bp, depending on the location of the primers.

RNA Preparation

Total RNA was extracted from Rabies virus infected (ERA strain) newborn mouse brain using RNAzol. The extracted total RNA was treated with RNAse-free DNAse I (Boehringer-Mannheim, Germany) at a concentration of 0.1 U/μg RNA for 30 minutes at 37° C. The DNAse I-treated RNA was purified using an RNeasy kit (Qiagen, Valencia, Calif.) per the manufacturer's instructions. Approximately 4 μg of DNAse 1-treated RNA was used for each reverse transcription reaction using 15-mer oligo-p(dT)$_{15}$ primers (Boehringer Mannheim, Germany) to produce reverse transcribed cDNA (RT-cDNA).

Reverse Transcription

The reverse transcription reactions were carried out in a 50 μl volume in an Eppendorf test tube comprising 10 μl 5X first strand buffer (250 mM Tris-HCl, pH 8.3, 375 mM KCl, 15 mM MgCl$_2$) (Gibco-BRL, Gaithersburg, Md.), 2.5 μl 10 mM each of ultra-pure dATP, dTTP, dGTP, and dCTP (Pharmacia Biotech, Rahway, N.J.), 4.5 μl 0.1 M dithiothreitol (DTT, Gibco-BRL), 0.5 μl RNAse inhibitor (400 U/μl, Boehringer-Mannheim, Germany), 2 μl oligo-p(dT)$_{15}$ primers (0.8 μg/μl Boehringer Mannheim, Germany), and 4 μl Supercript™ II RT enzyme (200 U/μl, Gibco-BRL). The reaction tube was incubated at 37° C. for 90 minutes.

One-hundredth volume (0.5 μl) of each reaction mixture comprising synthesized, double-stranded reverse transcribed cDNA (RT-cDNA) or 0.5 μl of the original total RNA sample were adsorbed onto a nylon membrane and used in SPADT using specific and non-specific forward and reverse primer pairs.

Solid-phase Matrix

The solid phase matrix consisted of strips of Hybond-N (Amersham Pharmacia Biotech) nylon membrane cut to a final size of 4×12 mm.

Multiarrays

Multiarrays were prepared using an Auto-spot Robot Asp 222, (Abimed, Analysen-Technik Germany), consisting of a computer driven robotics arm equipped with a syringe. Primers were suspended in water, containing phenol red at a final concentration of 0.01 mg/ml. Two hundred nanoliters of individual primers or primer pairs (forward and reverse) were spotted at final concentrations range from 0.1 pmole to 4 pmole.

UV Crosslinking

UV crosslinking was performed as described previously herein except that a UV dose of 120 mJ/cm$^2$ was used.

Template Amplification

In some experiments, 0.01 ng to 20 ng of double stranded DNA template in 10 μl of water was added to the nylon membranes containing the UV crosslinked primers and sandwiched between two coverslips for about 30 minutes. The wet membrane was then transferred to a microfuge tube containing the Taq polymerase reaction mixture. In other experiments, the nylon membrane contained only the UV crosslinked primers and 20 ng of DNA template were added to the Taq polymerase reaction mixture. Template amplification was carried out using a PTC-100 thermocycler (M.J. Research, Inc.). The 4×12 mm nylon filters with arrayed primers were inserted in a microfuge tube containing 200 μl of reaction mixture containing 20 mm Tris-HCl, pH 8.4, 50 mM KCl buffer, 2 mM MgCl$_2$, 0.2 mm each dNTP, Digoxigenin-11-2'-deoxy-uridine 5' triphosphate (alkali stable dUTP, Boehringer Mannheim Indianapolis, Ind.) and 8 μl (40 units) Platinum Taq DNA polymerase (Gibco/BRL Gaithersburg, Md.). Temperature cycling conditions for Taq polymerase amplification were: denaturation at 95° C. (1 minute), annealing at 55° C. (1 minute), extension at 72° C. (2 minutes). After 40 cycles, a final extension step at 72° C. (10 minutes) was carried out.

Hybond N was found to interfere with Taq polymerase activity irrespective of whether the PCR was carried out in solution or on solid phase. This interference was overcome by either adding more polymerase to the reaction, or by adding Triton X-100 to the reaction. Thus, either a high concentration of Taq polymerase (e.g., 4 μl of a 5U/μl stock solution of Taq giving approximately 20 units in 100 μl reaction volume), or a lower concentration of polymerase (e.g, 1 μl of polymerase at 5U/μl per 100 μl of reaction) coupled with 1% Triton X-100 in the reaction overcame this problem.

Detection of the Synthesized DNA Products on Solid-Phase

Detection of the synthesized DNA products on solid-phase was performed using the Genius 3 System Nonradioactive Nucleic Acid Detection Kit (Boehringer Mannheim, Indianapolis, Ind.) that detects Digoxigenin-labeled nucleic acids with an alkaline phosphatase conjugated anti-digoxigenin antibody followed by the NBT/BCIP colorimetric method. In brief, the nylon strips were incubated in blocking buffer (0.1 M nucleic acid, 0.15 M NaCl, pH 7.5, blocking reagent) for 3 minutes, followed by incubation for an additional 30 minutes in 1:500 diluted polyclonal sheep anti-digoxigenin antibody conjugated with alkaline phosphatase. The strips were washed twice in buffer without blocking reagent for 15 minutes for each wash. The NBT/BCIP color substrate solution was diluted to 1:50 dilution using buffer (100 mM Tris-HCl, 100 mM NaCl, 50 mM MgCl$_2$, pH 9.5). The color was developed for 15–30 minutes.

Scanning and Quantitative Analysis of the Multiarrays

The nylon strips containing the purple colored amplified products were scanned at 1200 dpi using an Astra 610S 30 bit scanner (Umax Technology, Inc., Fremont, Calif.) and Vista Scan 2.4 (Fremont, Calif.) and Adobe Photoshop 4.0 software (San Jose, Calif.). The scanned images were converted to inverted TIFF files and quantified utilizing Image Quant 1.2 software (Sunnyvale, Calif.). The buffer used for amplification of the solid-phase was routinely tested for the presence of amplified products by gel electrophoresis, any indication of leeching of the samples, or of carryover contamination. The buffer was routinely found to be negative for any such contaminants or events.

Demonstration of Specificity of Amplification

After colorimetric detection, the 4×12 mm nylon strips containing amplified products were hybridized to $^{32}$P-labeled diagnostic probes according to published methods (Yamada et al., 1989, Proc. Natl. Acad. Sci. USA 86:5123–5127). Briefly, after staining, the arrays were prehybridized for 2 to 5 hours in 5×SSC, 0.1% SDS, 5% Denhardt's solution and 100 μg/ml salmon sperm DNA at 50° C. followed by hybridization overnight with a $^{32}$P-labeled probe. The filters were washed in 6×SSC (1×SSC= 0.15 M NaCl, 0.015 M Na—Citrate, pH 7.0), 0.1% SDS, at 4° C. below the calculated melting temperature of the oligonucleotide probe being detected.

The Results of the experiments presented in this example are now described.

The ability to interrogate an uncharacterized DNA sample for the presence of scarce copies of foreign DNA, or to determine whether it contains unique members of a large gene family or one of many possible genetic rearrangements are long-felt needs which, until the present invention, have been unfilled. As stated previously elsewhere herein, the alternative of carrying out in parallel, hundreds of PCRs, each reaction containing primers specific for a defined gene sequence, is overly cumbersome, requiring highly specialized equipment and large amounts of reagents. The use of DNA chips containing microarrays of diagnostic probes is only suitable if the gene of interest is sufficiently abundant in the sample and the procedure involved is costly and requires multiple steps (cDNA synthesis, PCR amplification, hybridization) that make the procedure cumbersome. A more viable alternative would be to analyze a target DNA template using multiple sets of compartmentalized primer pairs anchored to a solid-phase. A solid-phase PCR that can exponentially amplify target DNA has not been reduced to practice until the disclosure of the present invention.

As previously discussed elsewhere herein, the present invention discloses methods for solid-phase amplification of a DNA template in a multiarray format in which superlinear amplification of the target DNA is accomplished once a sufficient primer pair density is achieved. The invention further discloses that amplification of a solid-phase adsorbed DNA template using anchored primers is not only achievable, but is also more efficient than amplification by solid-phase anchored primers of a DNA template in solution. Further, the solid-phase matrix/primers and detection instrumentation are all easily available and should facilitate the broad utilization of this approach.

Identification of Primers Suitable for Template Amplification in Solid-phase

UV-crosslinked oligonucleotide primers with a 20 mer T leader sequence could be reliably UV crosslinked to a nylon substrate and withstood over 40 thermocycles from 55° C. to 95° C. without being released into solution. In order to establish which UV crosslinked primers would be most efficient and the most specific for the amplification of a DNA target template, a solid-phase primer extension test in a multiarray format was employed. Two hundred nanoliters of each individual primers were arrayed at a 4 pmol concentration (500 μm diameter spots) were UV crosslinked to the Hybond-N membrane and were tested for their ability to extend a specific and a non-specific DNA template using 40 cycles of Taq polymerase reaction. The sequences of these primers are provided in Tables 1 and 2. The specific templates used were the glycoprotein gene of rabies virus (RGP) strain Evelyn Rokitniki Adelseth (ERA) and the p41 gene of HHV6 virus.

TABLE 2

| Target Code | SEQ ID NO: | Primer Sequence | Tm | GC (%) |
|---|---|---|---|---|
| p41 FH46 | 20 | 5'(20T)C GGG AAC ATA GAG AAA CGA G-3' | 61.7° C. | 50 |
| p41 FH92 | 21 | 5'(20T)T GAA AAG CTG GAA AAC TAT T-3' | 56.6° C. | 30 |
| p41 FH44 | 22 | 5'(20T)A TCG GGA ACA TAG AGA AAC G-3' | 61.1° C. | 45 |
| p41 FH429 | 23 | 5'(20T)C TGT GTG CAC GGA CAA GAA G-3' | 62° C. | 55 |
| p41 FH438 | 24 | 5'(20T)C GGA CAA GAA GTG GTG CGA G-3' | 64° C. | 60 |
| p41 FH373 | 25 | 5'(20T)C TAT ATA CGA GGG TTT TGG T-3' | 55.8° C. | 40 |
| p41 FH440 | 26 | 5'(20T)G ACA AGA AGT GGT GCG AGA C-3' | 61.9° C. | 55 |
| p41 FH549 | 27 | 5'(20T)C TCT GGT AAA TCT GAC GCT T-3' | 58.9° C. | 45 |
| p41 FH615 | 28 | 5'(20T)C GTG ACA GAG ATG AAT GAA C-3' | 57.1° C. | 45 |
| p41 FH694 | 29 | 5'(20T)C TAT CTG CCA AAA ATT TAC A-3' | 55.4° C. | 30 |
| p41 RH852 | 30 | 5'(20T)T TTG AGC TGT TCC TGA GTT A-3' | 57.5° C. | 40 |
| p41 RH886 | 31 | 5'(20T)C TTG TTT ACC CAT TCG TTC A-3' | 60.4° C. | 40 |
| p41 RH854 | 32 | 5'(20T)T CTT TGA GCT GTT CCT GAG T-3' | 58.8° C. | 45 |
| p41 RH567 | 33 | 5'(20T)A GCG TCA GAT TTA CCA GAG C-3' | 61.3° C. | 50 |
| p41 RH568 | 34 | 5'(20T)A AGC GTC AGA TTT ACC AGA G-3' | 58.9° C. | 45 |
| p41 RH829 | 35 | 5'(20T)A GGC TTC CAC CGT CAA CAA C-3' | 66.5° C. | 55 |
| p41 RH830 | 36 | 5'(20T)A AGG CTT CCA CCG TCA ACA A-3' | 67.1° C. | 50 |
| p41 RH598 | 37 | 5'(20T)G ATT AAC CTG TAC TAT AAT GTG C-3' | 55.7° C. | 35 |
| P41 RH598 | 33 | 5'(20T)C CTG TAC TAT AAT GTG CGC C-3' | 60.3° C. | 50 |
| p41 RH562 | 39 | 5'(20T)C AGA TTT ACC AGA GCG TTT A-3' | 57.7° C. | 40 |
| HHV8 FP1 | 40 | 5'(20T)A TGC CTG TGG ATT TTC ACT-3' | 59.1° C. | 42 |
| HHV8RP1191 | 41 | 5'(20T)T CAA ATC AGG GGG TTA AAT G-3' | 61.9° C. | 40 |
| RHYb575 | 42 | 5'TGT CTT CTA CCT ACT GCT CCA CTA A-3' | 64° C. | 44 |
| HHYb544 | 43 | 5'AAA GCG TCT GGT AAA TCT GAC GCT T-3' | 71° C. | 44 |

Because UV crosslinking is known to activate thymine bases in DNA which then covalently couple to primary amines present in the nylon (Church and Gilbert, 1984, Proc. Natl. Acad. Sci. USA 81:1991–1995), it was determined whether the presence of several thymidine residues in the coding sequence of the primers and, in particular, in the 3' portion of its sequence, was a factor affecting primer efficiency in solid-phase template amplification. Furthermore, since in a multiarray setting the primer extension by Taq polymerase needs to occur under the same cycling temperatures and the same $Mg^{2+}$ concentrations for all of the primer sets, the optimal physicochemical conditions for the efficient function of primers at a concentration of 2 mM $Mg^{2+}$ was determined. Given an annealing temperature of 55° C. and extension temperature of 72° C., the results of the repeated primer extensions are shown in FIG. 4A for the RGP primers and in FIG. 5A for the HHV6p41 primers. FIG. 4A discloses the relative performance of primers in extending a RGP DNA template or in extending a non-specific human genomic control DNA. The quantitation of the results shown (FIG. 4B) indicate that of the forward RGP primers tested, three primers (FR122, FR168 and FR285) were the most specific and efficient, FR122 being the most efficient. That is, these primers demonstrated the highest sensitivity with the best signal-to-noise ratio. Among the ten reverse primers tested, five primers (RR601, RR899, RR900, RR915, and RR601) were specific, and primer RR899 was the most efficient. The results indicate that approximately 30 to 40% of the primers so designed were capable of selectively primer extending the RGP template without crossreactivity with the non specific genomic template.

Figure 5B:
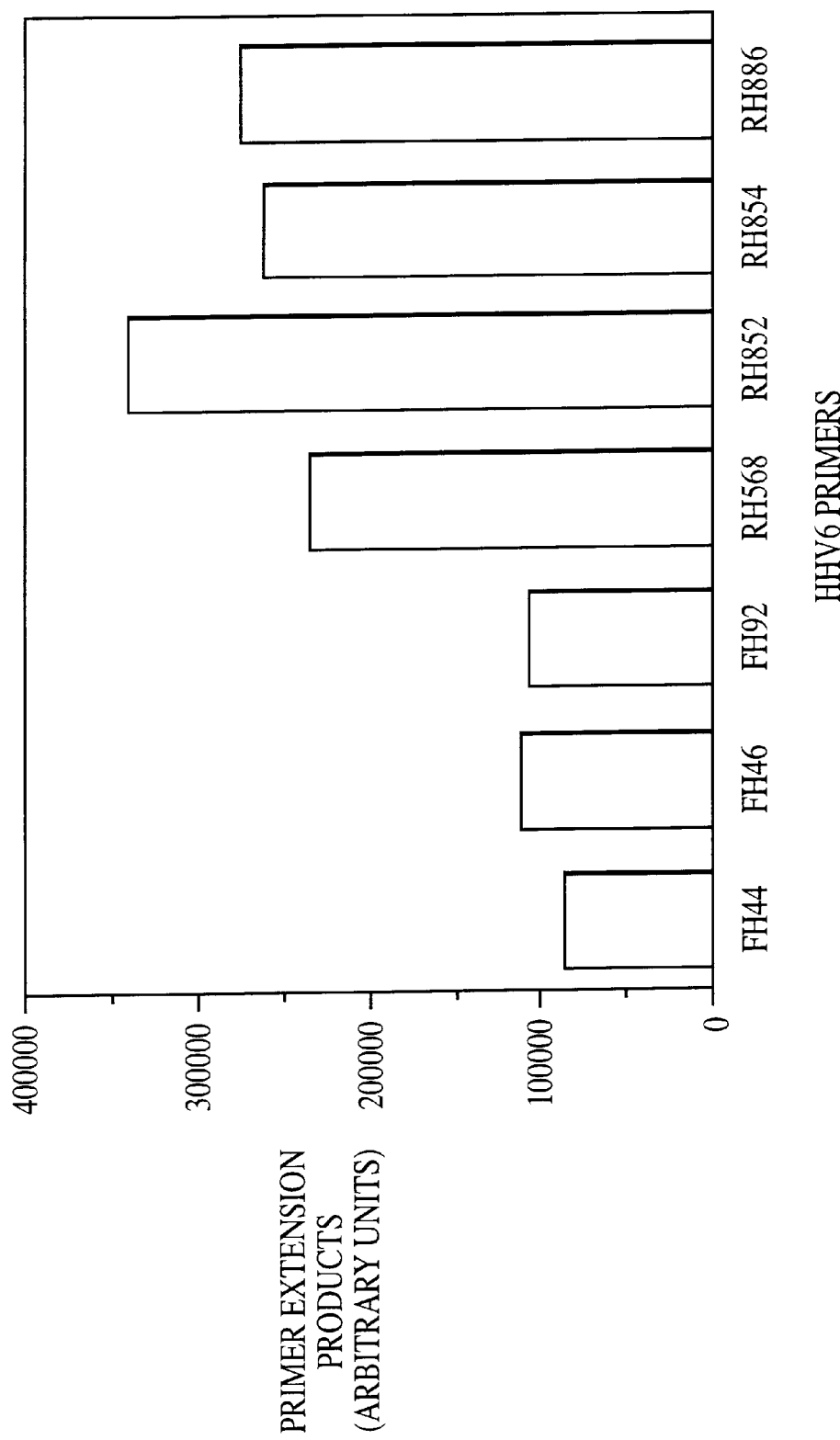
Figure 6A:
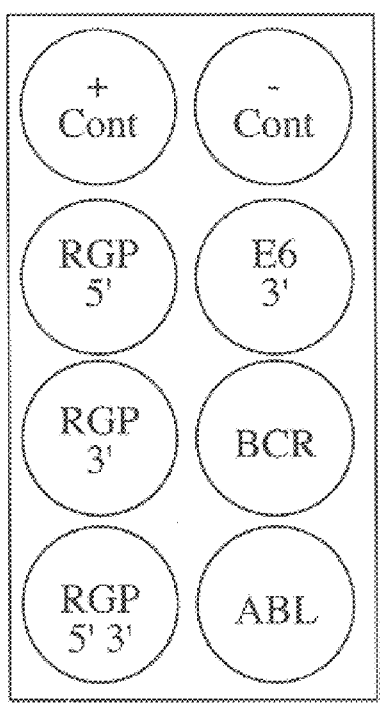
Figure 6B:
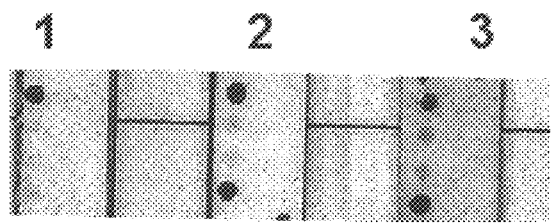

Utilizing the same approach to identify specific forward primers for HHV6p41, three often (FH44, FH46 and FH92) were identified as HHV6p41 specific primers (FIG. 5A), with FH46 being the best forward primer. Four of ten reverse primers (RH568, RH854, RH886, and RH852) were the most specific reverse primers with primer HHV RH852 being the best reverse primer (FIG. 5B). Further, the results indicate that approximately 30% to about 40% of the primers tested were specific for primer extension of the p41 HHV6 gene.

An analysis of the sequence of the primers (Table 2) disclosed that, under the specific conditions used, specificity and efficiency was achieved using primers (1) with a melting point from about 55° C. to about 59° C., (2) without GC rich sequences (GC boxes) in the 10 bp at the 3' end of the primers, and (3) that included two to four consecutive thymine bases at or near the 3' end of the primer which did not interfere with primer extension after UV-crosslinking. Without wishing to be bound by theory, the latter finding suggests that the relatively mild UV crosslinking conditions employed did not affect all of the thymidine residues present in the primers since the conditions were sufficient to efficiently crosslink the 15T leader sequence to the nylon but did not inhibit primer extension.

Solid-phase Amplification of DNA Template (SPADT) by Primer Pairs

The most efficient forward and reverse primers specific for the RGP template DNA sequence (FR122 and RR899, respectively) were arrayed either individually or as primer pairs at final concentrations ranging from 4 pmol to 0.5 pmol per spot. The arrays were subjected to amplification with Taq polymerase with the target DNA template in solution. The samples were examined after 10, 15, 20, 30, and 40 cycles. The results (FIG. 10A) indicate that matching forward and reverse primer pairs at the same final concentration amplified the template more efficiently than individual primers alone. Analysis of the intensity of the signal generated at different amplification cycles (FIG. 10B) indicated that such amplification did not have an exponential kinetics of template amplification (i.e., Amplification=Initial Concentration $(1+x)^n$ where $x \leq 1$) but rather superlinear kinetics were observed. The plateau of intensity of signal after forty cycles was due, in part, to the limits of the cholorimetric system used herein. That is, the colorimetric quantitation method used herein has an inherent, limited range of linearity and allows only an accurate evaluation of nucleic acid concentration present based on intensity of color development over the first approximately 20 cycles of the amplification process (FIG. 10B). Extrapolating the values obtained during the first fifteen cycles of amplification, the calculated value of x was about 0.4 when primer concentration was 4 pmol and the value decreased as primer concentration decreased.

SPADT is more Efficient when the DNA Template is Bound to the Solid Support

Nylon filters tend to bind undenatured double stranded DNA efficiently but the DNA does not remain stably bound in contrast to DNA which has been UV-crosslinked to the filter (Reed and Mann, 1985, Nucl. Acids Res. 13:7207–7221). In order to determine whether adsorbing the template DNA would affect the efficiency of solid-phase amplification, amplification of DNA adsorbed onto the nylon filter was compared to amplification of the same amount of DNA performed in solution as described previously elsewhere herein (e.g., in Example 1, supra).

Figure 11B:
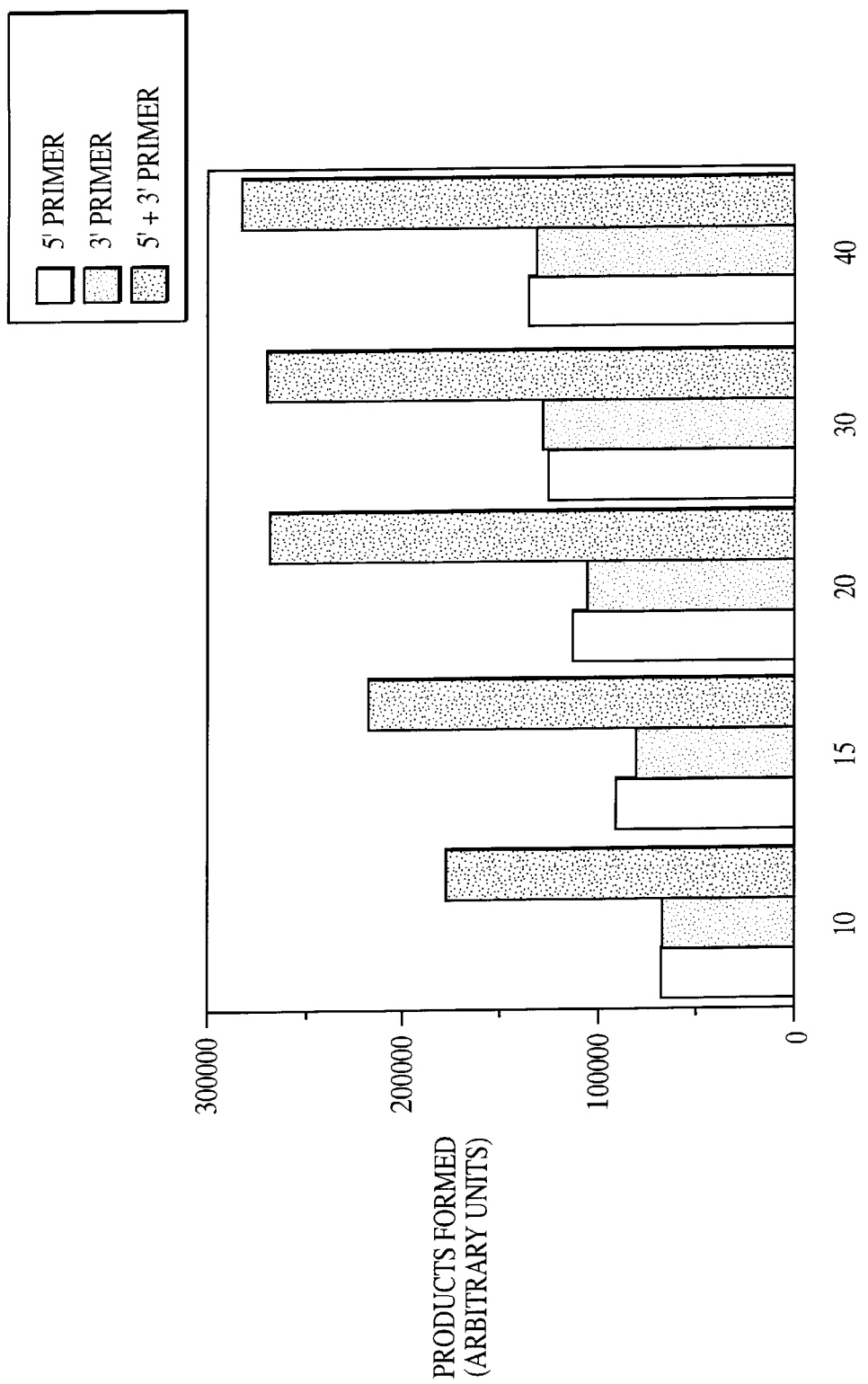

The results of the comparison which are depicted in FIGS. 10A and 11A, demonstrate that amplification of adsorbed target DNA template by arrayed primers is more efficient than the amplification of the same DNA template performed in solution. That is, samples of adsorbed DNA template (FIG. 11A) gave a stronger signal than samples of template DNA in solution (FIG. 10A) in the same number of cycles of amplification without an increase in non-specific background staining. The results illustrated in FIGS. 10A and 11A for samples where 4 pmol of primers were bound to the solid support were quantitated after scanning the arrays, magnifying the images using Adobe Photoshop, and analyzing the data using ImageQuant software all as previously described elsewhere herein. The data are disclosed in FIGS. 10B for template DNA in solution and in FIG. 11B for solid phase. The data disclosed herein demonstrate that a higher signal was detected when the DNA template was adsorbed on the solid support compared with the signal detected when the DNA template was in solution at all cycle points examined (i.e., samples were taken after 10, 15, 20, 30, and 40, amplification cycles). Additionally, the data disclosed herein in FIGS. 10A, 10B, 11A, and 11B, demonstrate that the amplification reaction demonstrated superlinear kinetics of amplification when both forward and reverse primers are present whether the template DNA is adsorbed or in solution, with an x value of about 0.5 that is superior to the values observed with the DNA template in solution.

In order to determine whether the adsorbed DNA remained bound to the solid support during thermocycling, $^{32}$P-labeled DNA was used as the template DNA and was adsorbed to the nylon filter. The filter was then subjected to 40 cycles in a Thermocycler and the amount of radioactivity released from the filter into the reaction buffer was monitored. The radioactivity released from the filter demonstrated that DNA was progressively released from the filter and, after 40 cycles, approximately 50% of the DNA was present in solution. Additional experiments using adsorbed DNA template indicated that the efficiency of amplification decreased when double stranded template DNA was UV-crosslinked to the nylon filter. Without wishing to be bound by theory, these data suggest that the increased efficiency of amplification of adsorbed template DNA is due to a higher DNA concentration at the solution/solid-phase interface than the concentration that could be achieved by DNA template in solution.

Limit of Detection of SPADT

The sensitivity limits of SPADT were determined using decreasing concentrations of RGP plasmid DNA template adsorbed to nylon filters and with matching forward and reverse primers UV-crosslinked to the surface. RGP DNA template ranging in amount from 10 ng to about 10 pg, was adsorbed onto Hybond-N containing UV-crosslinked arrays of matching forward (FR122) and reverse (RR899) primer pairs ranging in concentrations from about 4 pmol to about 0.1 pmol. The results demonstrate that 10 pg of template DNA were detectable after 40 amplification cycles of SPADT using 4 pmol of both primers (FIG. 9).

Further, in order to determine whether the addition of irrelevant DNA affected the sensitivity of the assay, 100 to 500 pg of human genomic DNA was added to each sample. The results, as show in FIG. 12, demonstrate that high concentrations of irrelevant DNA markedly interfere with the detection sensitivity of the SPADT assay. In the presence of 100 ng of irrelevant human DNA, the detection of 10 pg of specific RGP DNA was less efficient (FIG. 12, row C). The best conditions for detection sensitivity were achieved when 0.3% Triton X-100 and 3% DMSO were added to the reaction mixture. These changes permitted the use of Taq polymerase at the reduced concentration of 5U (2 $\mu$l) per 200 $\mu$l reaction mixture. When Taq polymerase was added at the beginning of the reaction and again after 25 cycles, RGP DNA could be detected at the level of 1 pg/sample after 40 cycles. When RGP DNA was mixed with 100 ng of human DNA, it was still detectable even at the concentration of 1 pg/sample (FIG. 9).

Specificity of SPADT Products

Figure 13A:
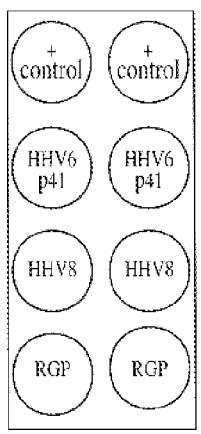
Figure 13B:
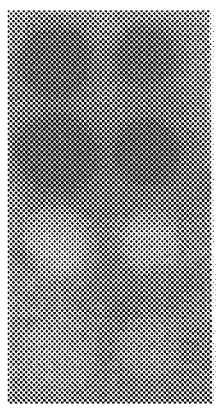
Figure 1:
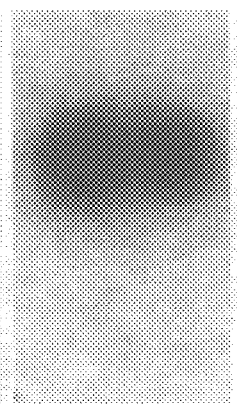
Figure 2:
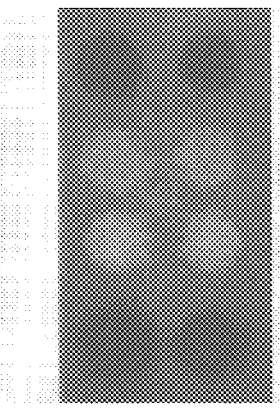
Figure 13C:
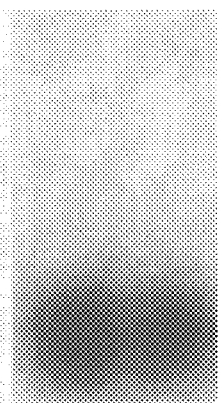
Figure 14A:
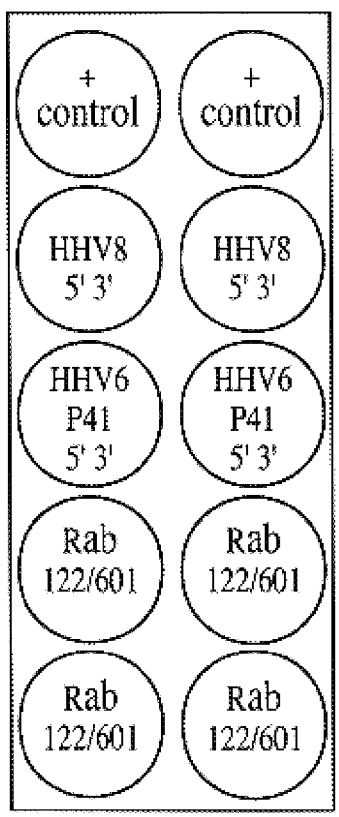
Figure 1:
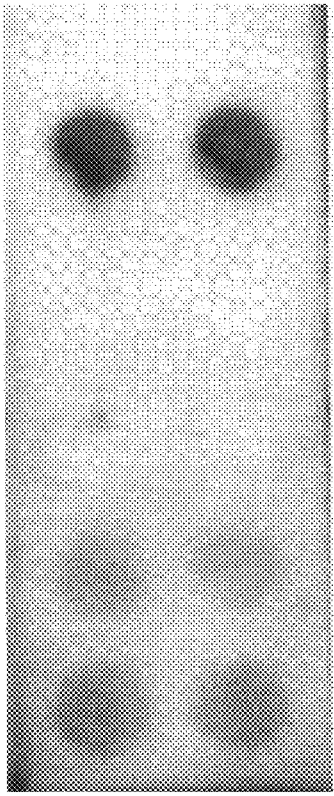
Figure 2:
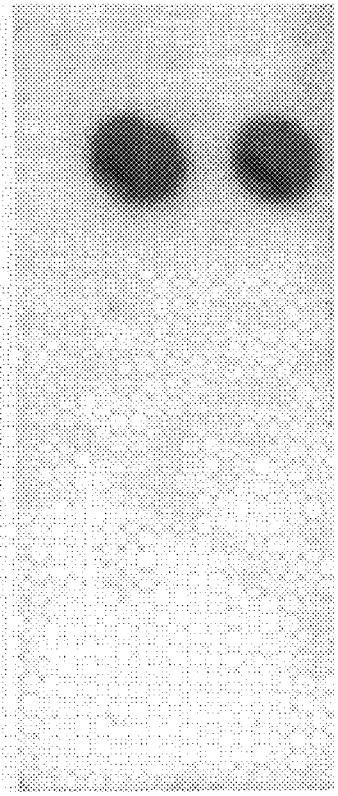

To determine the specificity of the product amplified in solid-phase superlinear DNA amplification, Hybond-N strips containing an array of matching forward and reverse primer pairs specific for RGP, HHV6-p41 and for HHV8 were tested in the colorimetric method as previously described herein. Further, the array was tested for specificity by hybridization to radiolabeled probes specific for each template DNA, i.e., one probe was specific for RGP120 and another for HHV6-p41 but neither probe bound to HHV8 (FIG. 13). The data disclosed herein demonstrate that the SPADT reaction is highly specific and that the primers were extended with high fidelity as demonstrated by the stringent hybridization of each probe only to the amplification product produced when SPADT was performed using the specific primer pair and its homologous template DNA (i.e., 10 ng of either RGP or HHV6 as adsorbed DNA template). That is, the radiolabeled probe for RGP only bound amplification products produced by SPADT using RGP primer pairs and RGP template and, similarly, the probe specific for HHV6p41 bound only amplification products produced by the combination of HHV6p41 primer pairs and HHV6p41 template DNA. Neither probe bound amplification products produced using HHV8 primer pairs and HHV8 template DNA further demonstrating that the specificity of SPADT depends on the identity of the primers and their homology to the template DNA and the homology of the probe to a sequence present within the template DNA bounded by the primer pairs.

SPADT using Reverse Transcribed cDNA or RNA as Template

The ability to use RNA or reverse transcribed cDNA (RT-cDNA) as a template in SPADT was also examined. Total RNA was isolated from Rabies virus infected mouse brain. The isolated total RNA was reverse transcribed using oligo-p(dT)15 primers. Equal amounts of total RNA and RT-cDNA were reversibly adsorbed onto the nylon membrane and used as templates in SPADT using both specific and non-specific forward and reverse primer pairs irreversibly bound to the membranes in order to determine the sensitivity and specificity of these two nucleic acid samples as templates in SPADT.

The data disclosed herein demonstrate that SPADT using RT-cDNA detected a target nucleic acid in a complex sample (i.e., rabies virus gp120 message in RNA isolated from mouse brain) specifically without cross reacting with non-specific primers. However, use of total RNA without reverse transcribing did not allow the detection of a specific, or non-specific, amplification product. Thus, total RNA may be interrogated using SPADT by simply reverse transcribing the RNA using oligo dT primers. The RT-cDNA is then simply adsorbed onto the solid support and interrogated as described previously elsewhere herein. Therefore, cDNA bound to nylon filters acted as a template and was specifically amplified by rabies-specific primers bound to solid phase.

The data disclosed herein demonstrate the conditions for a novel method of interrogating a nucleic acid sample for the presence of specific low-abundance genetic information. These data establish that solid-phase superlinear amplification of DNA template can be used when multiple amplification reactions are required to detect specific genes in a fraction of a cell population. Without being limited any particular use(s), an example of the potential use for this invention is the identification of one or multiple viruses or bacteria present in a biological sample. In a single step, SPADT combines target DNA template amplification with the specificity of detection of amplified products thereby accelerating and simplifying the detection process. The data disclosed demonstrate that superlinear amplification using forward and reverse primer pairs in the presence of sufficient forward and reverse primer concentrations. Such superlinear amplification is suitable to detect a target sequence present in picogram amounts.

The SPADT of the present invention utilizes multiarrays of highly specific forward and reverse primer pairs UV-crosslinked to Hybond-N nylon membranes. Relatively mild conditions were used in UV-crosslinking the approximately 20T leader sequence to the nylon without inhibiting primer extension, even when one to four Ts were present near the 3' end of the primer. Under the UV-crosslinking conditions disclosed herein, the multiple thymidine bases are activated and form covalent bonds with primary amines in the nylon (Church and Gilbert, 1984, Proc. Natl. Acad. Sci. U.S.A. 81:1991–1995). The density of oligonucleotides on a solid phase surface has been estimated to range from about 0.1 pmol/mm$^2$ on glass to about 10 pmol/mm$^2$ on aminated polypropylene (Southern and Shchepinov, 1999, Nature Genet. 21:5–9). The conditions disclosed herein were within these ranges and ensured amplification of DNA templates shorter than the about 700–800 bp target sequences examined herein. Without wishing to be bound by theory, the superlinear amplification observed herein may be explained by the accessibility of the complementary reciprocal primers to newly extended DNA strands. Less than optimal exponential amplification of the target template, on the other hand, likely reflects, without wishing to be bound by theory, the relatively restricted availability of the newly synthesized strand bound to the solid phase to hybridize to the complementary primers present nearby.

Figure 15:
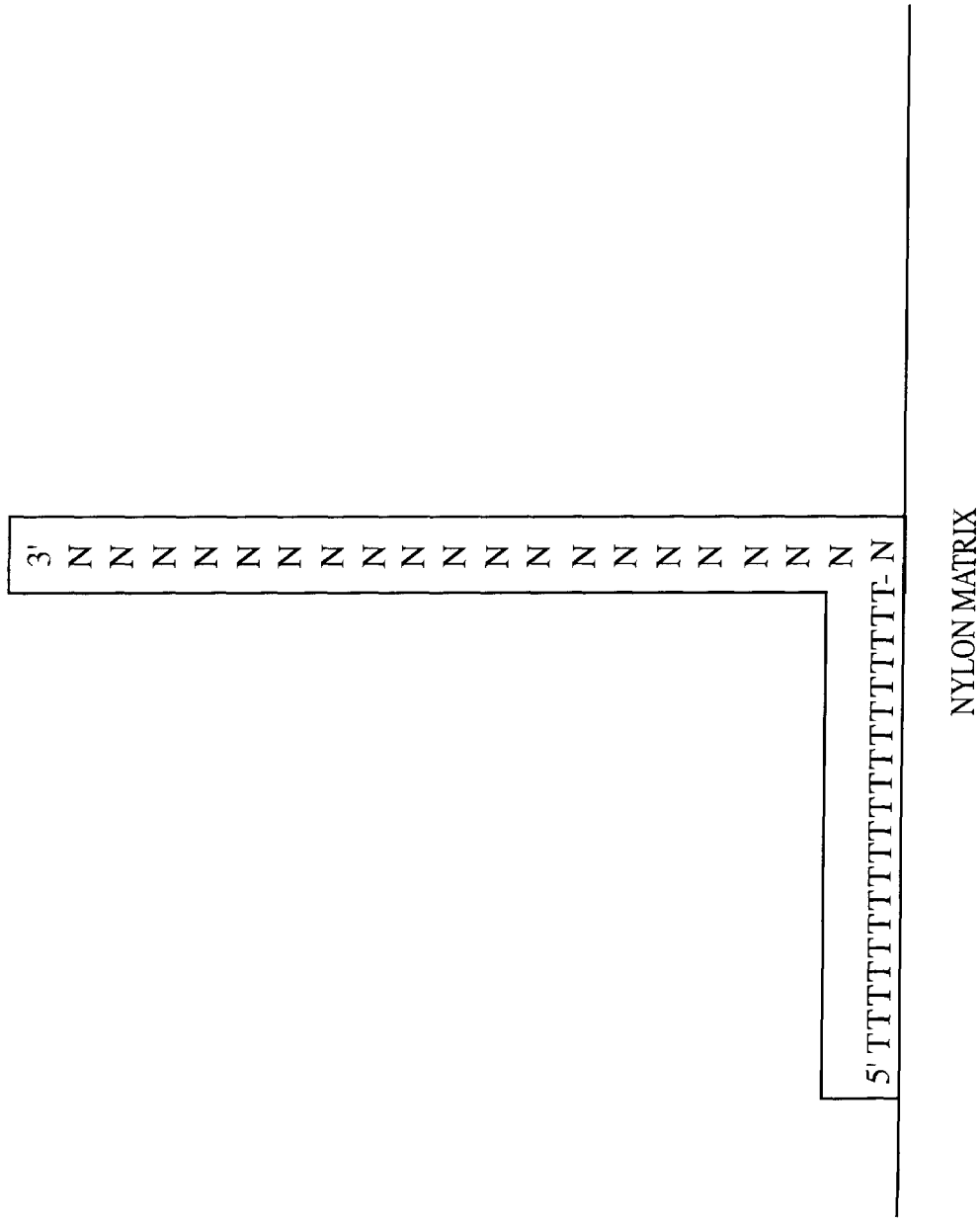
FIG. 15 is a drawing depicting the forward and reverse primers hypothetically bound to nylon matrix by UV crosslinking through poly-T leader sequence where N is A, T, G, or C.
Figure 16:
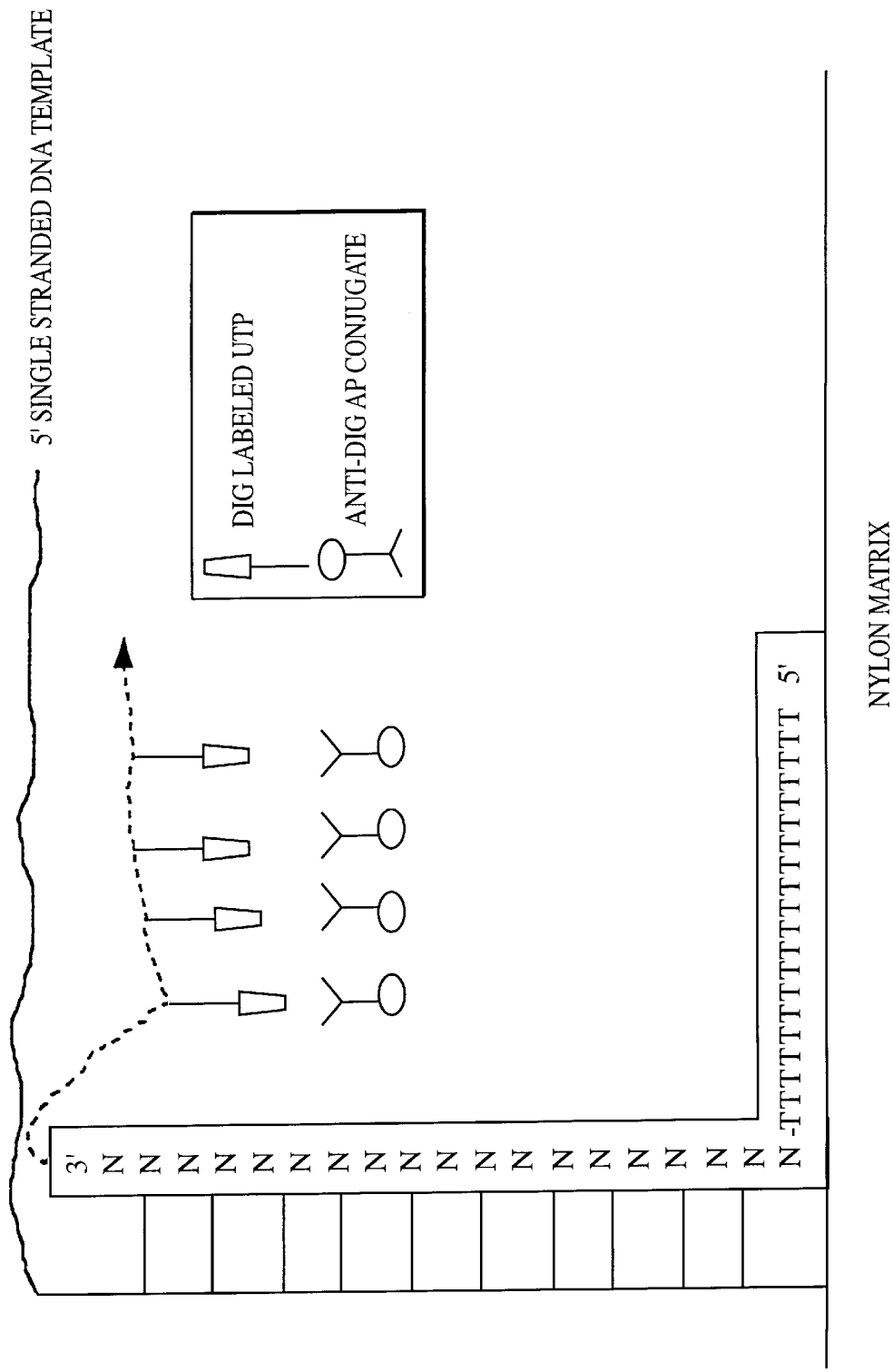
FIG. 16 is a drawing depicting hypothetical extension from a 5' primer bound to solid phase with DNA template in solution also depicting the dioxigenin-based detection of bound amplification product.
Figure 17:
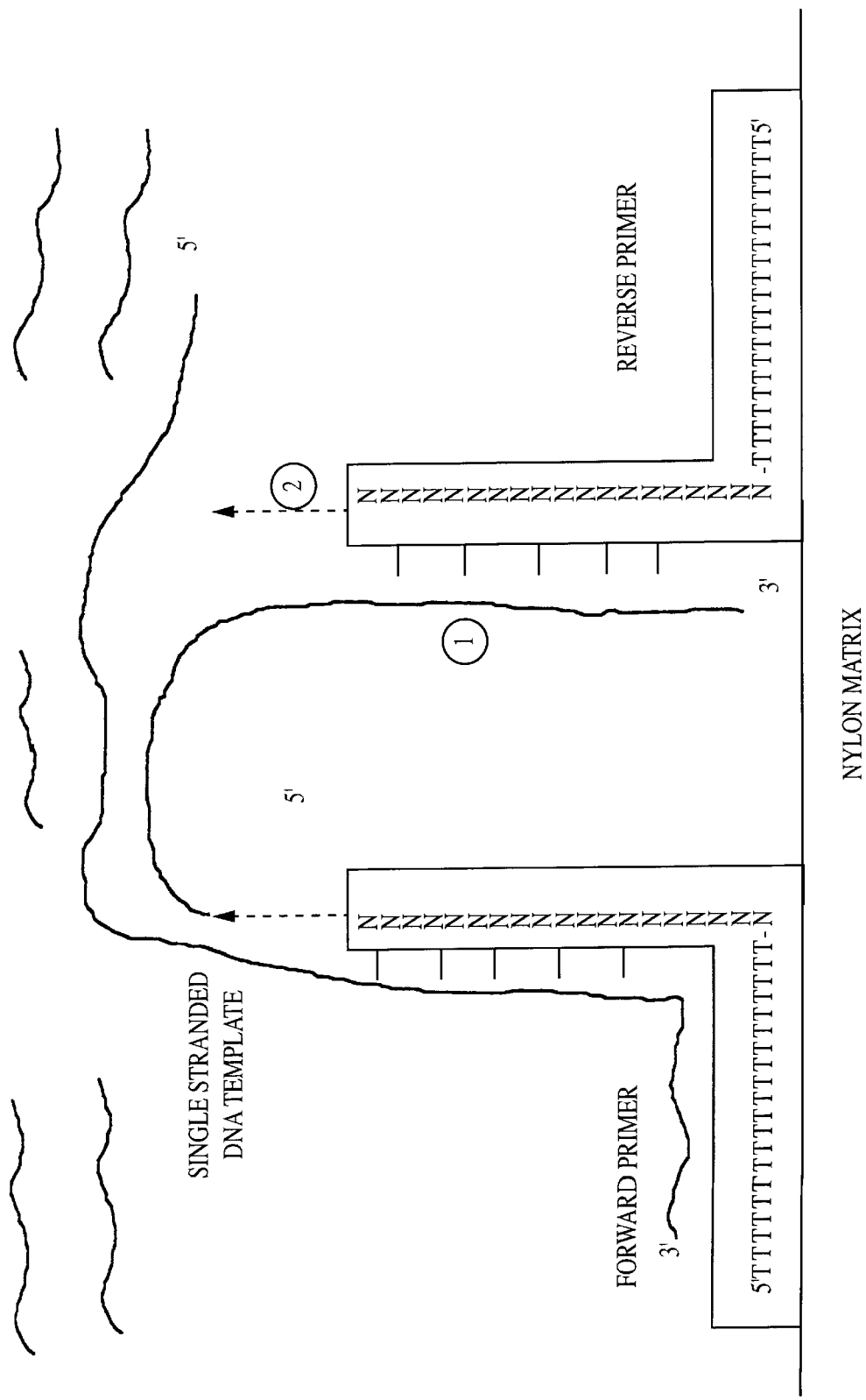
FIG. 17 is a drawing depicting hypothetical template amplification (1) using both forward (3) and reverse (2) primers bound to the solid phase (nylon matrix) with DNA template in solution.
Figure 18:
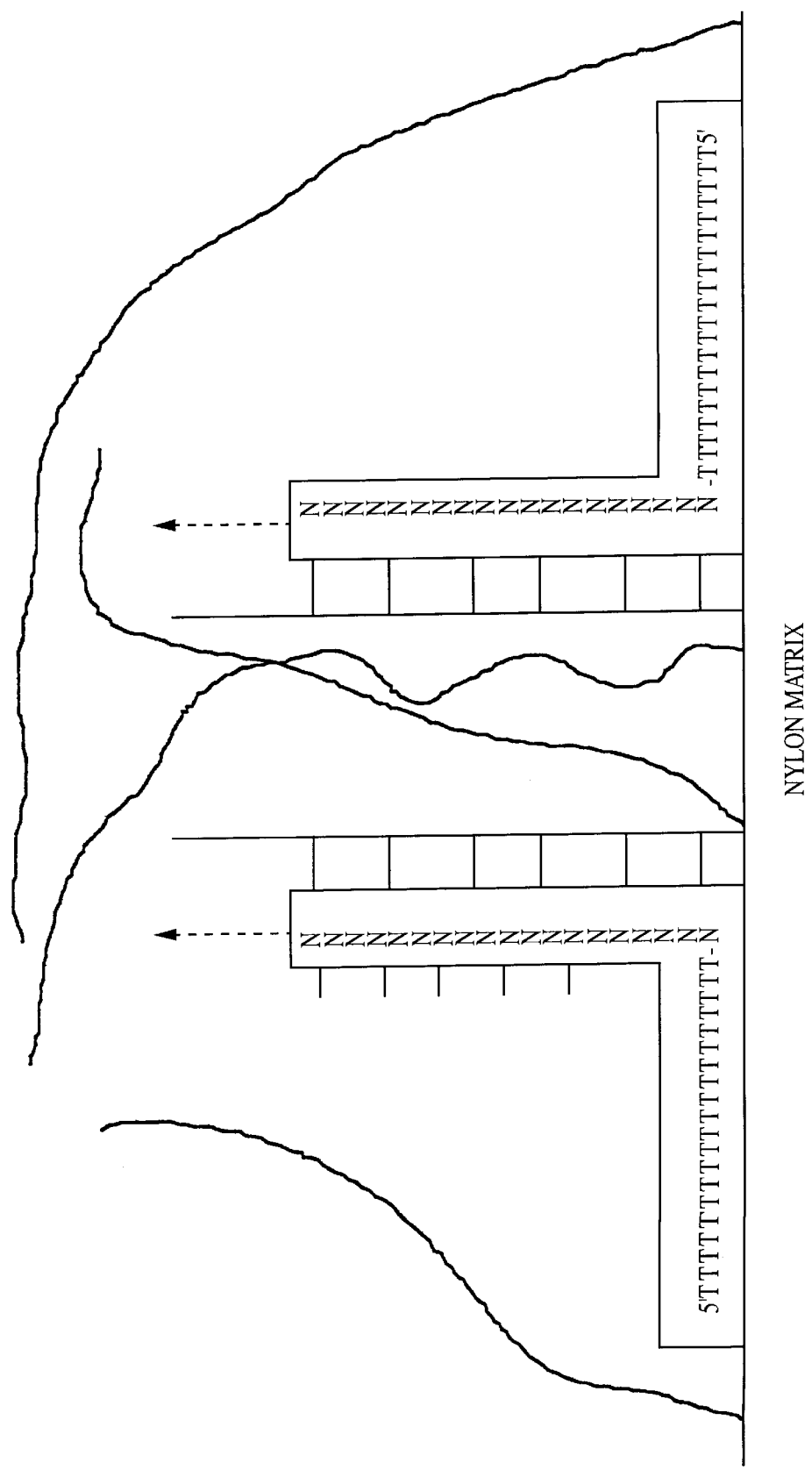
FIG. 18 is a drawing depicting hypothetical template amplification of both forward and reverse primers bound to the solid-phase (Nylon Matrix) with the DNA template also bound to the solid phase.

Without wishing to be bound by theory, FIGS. 14 through 17 depict several possible interactions and/or configurations of the various components during SPADT amplification. FIG. 15 depicts the binding of a poly dT primer to a nylon matrix where the primer comprises a 20 mer poly dT sequence covalently linked to a 20 mer sequence homologous to a specific nucleic acid of interest. A hypothetical extension of a single primer bound to a nylon matrix with the DNA template in solution is shown in FIG. 16. The figure further depicts the immunological detection of amplification product using a digoxigenin-labeled dUTP and anti-Dig conjugate to an enzyme such as alkaline phosphatase such that addition of a chromogenic substrate results in a colorimetric reaction which localizes to the nylon matrix. FIG. 17 depicts DNA template amplification using both forward and reverse primers bound to the nylon matrix with the DNA template in solution. Further, FIG. 18 depicts SPADT amplification wherein both forward and reverse primers are irreversibly bound to the nylon matrix and where DNA template is adsorbed to the matrix as well.

One challenge in developing diagnostic multiarrays is the requirement for highly specific primers that can all function efficiently under the same cycling conditions and at the same $K^+$ and $Mg^{++}$ concentrations. The data disclosed herein demonstrate an approach to designing specific primers for viral genes in which the specificity of the primers can be defined experimentally by comparing multiple primer extensions of the specific target sequences versus non-specific DNA. This approach has led to the discovery of several general rules for the successful design of primers for use in multiarrays. First, the data disclosed herein demonstrate that primers with similar melting points and a GC content ranging from about 40% to about 60% can be used in one reaction (Lowe et al., 1990, Nucleic Acids Res. 18:1757–1761). Second, the data disclosed herein demonstrate the importance of the absence of GC boxes (i.e., 4–5 GC) near the 3' end of the primer in designing primers that are UV-crosslinked to a nylon matrix and that require high specificity of sequence recognition. Third, it is crucial when targeting mammalian genes by solid-phase amplification, to demonstrate that each primer pair is truly specific for the target DNA sequence.

Adsorbed DNA template generated more abundant amplification products than did DNA template in solution. Further experiments indicated a decrease in the efficiency of amplification where the DNA template was UV-crosslinked to the substrate. Without wishing to be bound by theory, the increased efficiency of amplification of adsorbed DNA template may reflect the relatively higher DNA concentration at the solution/solid-phase interface than the concentration achievable by DNA template in solution. The Hybond-N nylon matrix used herein efficiently adsorbs double-stranded DNA template (Reed and Mann, 1985, Nucleic Acids Res. 13:7207–7221). This cannot be achieved with a glass matrix. Thus, a nylon matrix appears to be preferable to other solid-phase matrices (such as glass, silicon, or plastic) for efficient SPADT. Although the experiments disclosed herein involve double-stranded template DNA, single stranded DNA, like cDNA derived from reverse-transcription of mRNA, may also be used as a template.

The data disclosed herein demonstrate that the digoxigenin-labeled amplified product may be visualized on the solid support as discrete spots that can be retained for permanent records. The concentration of digoxigenin-labeled dUTP and the development time must be strictly maintained at the conditions described herein to avoid high color background of the filters. This detection method, which is simple and inexpensive, has the advantage of being readable with widely available instrumentation (e.g., a desktop computer and a computer scanner) and software (e.g., Adobe Photoshop and Image Quant). Alternative and more efficient detection methods using, for example, a fluorescence or chemiluminescence step, can be used but requires more expensive and specialized instrumentation for detection of the amplified product(s).

The data disclosed herein demonstrate the specificity of the amplified product which was confirmed by hybridization to specific radiolabeled probes after colorimetric detection of the amplified signal. Such a hybridization step is not desirable on a routine basis since it is time-consuming and cumbersome. Moreover, the need for a hybridization step to confirm the identity of the amplification product(s) may be avoided by examining multiple target sequences for each gene under investigation thereby eliminating potential artifacts with redundant confirmation. This approach is particularly useful for foreign sequences such as those of viruses and bacteria that contain multiple genes.

A theoretical version of solid-phase PCR using bound forward and reverse primers and in solution DNA template has been proposed in "bridge" PCR (Adams and Kron, 1997, U.S. Pat. No. 5,641,658). The SPADT method disclosed herein differs fundamentally from the "bridge" PCR technology in that not only the primer pairs but the DNA template are bound to the solid substrate, thereby drastically increasing the efficiency of the reaction compared with conditions in which DNA template is in solution. Moreover, SPADT using unmodified primers, which are readily available commercially, with a very inexpensive solid-phase matrix, enhances the detection sensitivity by modification of the buffer system. Most important from an economical point of view, the SPADT of the present invention uses a method of detection and quantitation that does not require expensive instrumentation. Using the methods disclosed herein, it is possible to array 5–10 nl of primer solution on a nylon matrix in spots with less than 500 $\mu$m of spacing. In addition, both sides of the nylon matrix can be used, effectively doubling the number of potential questions that can be addressed to interrogate a small DNA sample. The nylon matrix allows the use of primers that do not require expensive modifications before use. Initially, a disadvantage of the nylon matrix was its inhibitory effect on Taq polymerase enzyme activity so that 4-fold the usual concentrations of Taq were required for an efficient amplification reaction. Without wishing to be bound by theory, the inhibition was probably due to adsorption of enzyme to the membrane since a Triton X-100 concentration of 0.1% was sufficient to fully restore the Taq polymerase enzyme activity at concentration comparable to those used for PCR in solution. Furthermore, the use of 3% DMSO increased the sensitivity of detection by improving specificity of amplification (Varadaraj and Skinner, 1994, Gene 140:1–5).

The advantages of SPADT over conventional solution PCR are threefold: 1) SPADT obviates the need for hundreds of parallel reactions when the goal is detection of which foreign genes are present among hundreds of possible target genes; 2) crosslinking of both the forward and reverse primers to a solid support avoids the competition between different sets of primer pairs commonly observed in multiplex PCR; and 3) the DNA template adsorbed to solid-phase allows for relatively high concentrations of DNA using small DNA samples. Most of the currently available procedures for detection of scarce DNA sequences are not suitable for high throughput screening since they involve multiple PCR, electrophoresis, radioisotopes and/or centrifugations. Although methods for detecting different expressed gene sequences in the multiarray format on DNA chips are now available (Lockhart et al., Nature Biotechnol. 14:1675–1680; Castellino, 1997, Genome Res. 7:943–946; Kricka, 1998, Nature Biotechnol. 16:513–514), this approach is prohibitively expensive for routine diagnostic tests and often the procedure is not sufficiently sensitive. Thus, the present invention provides a novel, rapid, efficient and cost-effective procedure for detecting low-abundance genetic information in a complex biological sample.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting the presence or absence of a specific nucleic acid in a sample comprising DNA, said method comprising performing an amplification reaction, wherein a solid support on which a 5' and a 3' primer are irreversibly bound and said DNA is absorbed such that it is reversibly bound, is incubated under amplification conditions, and determining whether said specific nucleic acid is amplified, wherein when said specific nucleic acid is amplified, said specific nucleic acid is present in said sample and when said specific nucleic acid is not amplified, said specific nucleic acid is not present in said sample.

2. The method of claim 1, wherein said solid support comprises a solid to which said DNA cannot be irreversibly bound upon adding said DNA to said solid support in the absence of any further reaction.

3. The method of claim 2, wherein said solid support is selected from the group consisting of a nylon membrane, and a nitrocellulose membrane.

4. The method of claim 3, wherein said solid support is a nylon membrane.

5. The method of claim 1, wherein said primers are irreversibly bound to said solid support by UV-crosslinking said primers to said support.

6. The method of claim 1, wherein said 5' and 3' primers further comprise a poly-thymidine sequence at their 5' ends.

7. The method of claim 6, wherein said poly-thymidine sequence comprises from about 15 to about 80 thymidine nucleotides.

8. The method of claim 7, wherein said 5' and 3' primers comprise a sequence homologous to the sequence of said specific nucleic acid, said primers ranging in length from about 19 nucleotides to about 23 nucleotides.

9. The method of claim 1, wherein when said primers are in double stranded form, the thermal melting temperature of said double stranded form of said primers is in the range of about 55° C. to about 65° C.

10. The method of claim 8, wherein said 5' and 3' primers are lacking a GC rich region at the 3' end of said 5' and 3' primers.

11. The method of claim 1, wherein said amplification is performed by a reaction selected from the group consisting of a polymerase chain reaction, and a ligase reaction.

12. The method of claim 1, wherein said determination of whether said specific nucleic acid is amplified is performed by incorporating a detectable label into said amplified nucleic acid during amplification and detecting said label.

13. The method of claim 1, wherein said amplification conditions comprise about 2 mM $MgCl_2$ and about 50 mM KCl.

14. The method of claim 1, wherein said specific nucleic acid is selected from the group consisting of a nucleic acid comprising a mutation, a nucleic acid comprising a mutation in a cancer gene, and a nucleic acid comprising a sequence present in the genome of an infectious agent.

15. A method of determining the presence or absence of expression of a specific nucleic acid in a cell, said method comprising reverse transcribing RNA obtained from said cell to produce DNA, performing an amplification reaction, wherein a solid support on which a 5' and a 3' primer are irreversibly bound and said DNA is adsorbed such that it is reversibly bound is incubated under amplification conditions, and determining whether said DNA is amplified, wherein when said DNA is amplified, said specific nucleic acid is expressed in said cell and when said DNA is not amplified, said specific nucleic acid is not expressed in said cell.

16. A method of determining the presence or absence of a specific RNA molecule in a sample, said method comprising reverse transcribing said RNA to DNA, performing an amplification reaction wherein a solid support on which a 5' and a 3' primer are irreversibly bound and said DNA is adsorbed such that it is reversibly bound is incubated under amplification conditions, and determining whether said DNA is amplified, wherein when said DNA is amplified, said specific RNA is present in said sample, and when said DNA is not amplified, said specific RNA is not present in said sample.

17. The method of claim 16, wherein said specific RNA is viral RNA.

18. A method of designing a primer which amplifies a specific nucleic acid provided said specific nucleic acid is present in a sample comprising DNA, said method comprising (a) synthesizing at least one 5' and one 3' primer homologous to said specific nucleic acid;

(b) performing an amplification reaction wherein a solid support on which said primer is irreversibly bound and said DNA is absorbed such that it is reversibly bound is incubated under amplification conditions to generate an amplified nucleic acid;

(c) determining the specificity of said primer by comparing the ability of said primer to produce a detectable amount of said amplified nucleic acid in said amplification reaction in the presence or absence of said specific nucleic acid, wherein a detectable amount of amplified nucleic acid in said amplification reaction in the presence of said specific nucleic acid, compared with the absence of a detectable amount of said amplified nucleic acid in the absence of said specific nucleic acid, is an indicator that said primer is specific for ampliyfing said specific nucleic acid;

(d) comparing the characteristics of said primers of step (c) which are specific for said specific nucleic acid to identify common features shared among the most specific of said primers; and (e) synthesizing an additional primer incorporating said features identified in step (d), thereby designing a primer which amplifies a nucleic acid provided said specific nucleic acid is present in a sample comprising DNA.

19. The method of claim 18, wherein said comparing step (d) is performed using an algorithm.

\* \* \* \* \*

SEQUENCE LISTING

```
<160> NUMBER OF SEQ ID NOS: 43

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence:Primer RGP
      FR 164

<400> SEQUENCE: 1
tttttttttt tttttttttt atttggtagt ggaggacgaa gga                           43

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Primer RGP
      FR165

<400> SEQUENCE: 2
tttttttttt tttttttttt tttggtagtg gaggacgaag                               40

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Primer RGP
      FR122

<400> SEQUENCE: 3
tttttttttt tttttttttt cctggaggcc gattgacata c                             41

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Primer RGP
      FR285

<400> SEQUENCE: 4
tttttttttt tttttttttt ggctgaaacc tacactaact                               40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Primer RGP
```

FR168

<400> SEQUENCE: 5
tttttttttt tttttttttt ggtagtggag gacgaaggat                          40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Primer RGP
        FR273

<400> SEQUENCE: 6
tttttttttt tttttttttt cgttgtgacg gaggctgaaa                          40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Primer RGP
        FR336

<400> SEQUENCE: 7
tttttttttt tttttttttt aaagcatttc cgcccaacac                          40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Primer RGP
        FR170

<400> SEQUENCE: 8
tttttttttt tttttttttt tagtggagga cgaaggatgc                          40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Primer RGP
        FR166

<400> SEQUENCE: 9
tttttttttt tttttttttt ttggtagtgg aggacgaagg                          40

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Primer RGP
        RR855

<400> SEQUENCE: 10
tttttttttt tttttttttt caactgatcg ggagggcacc att                      43

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Primer RGP
        RR899

<400> SEQUENCE: 11
tttttttttt tttttttttt acaaggtgct caatttcgtc         40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Primer RGP
      RR797

<400> SEQUENCE: 12
tttttttttt tttttttttt ccatccataa gtctaagtcc         40

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: Primer RGP
      RR601

<400> SEQUENCE: 13
tttttttttt tttttttttt ggttagtgga gcagtaggta ga         42

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Primer RGP
      RR900

<400> SEQUENCE: 14
tttttttttt tttttttttt aacaaggtgc tcaatttcgt         40

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Primer RGP
      RR915

<400> SEQUENCE: 15
tttttttttt tttttttttt gaccaactcc tctacaacaa         40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: PrimerRGP
      RR713

<400> SEQUENCE: 16
tttttttttt tttttttttt acaaagccgc aagtctcact         40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Primer RGP
      RR715

-continued

```
<400> SEQUENCE: 17
tttttttttt tttttttttt ctacaaagcc gcaagtctca                        40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Primer RGP
      RR719

<400> SEQUENCE: 18
tttttttttt tttttttttt tcatctacaa cgcagcaagt                        40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Primer RGP
      RR720

<400> SEQUENCE: 19
tttttttttt tttttttttt ttcatctaca aagccgcaag                        40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Primer p41
      FH46

<400> SEQUENCE: 20
tttttttttt tttttttttt cgggaacata gagaaacgag                        40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Primer p41
      FH92

<400> SEQUENCE: 21
tttttttttt tttttttttt tgaaaagctg gaaaactatt                        40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Primer p41
      FH44

<400> SEQUENCE: 22
tttttttttt tttttttttt atcgggaaca tagagaaacg                        40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Primer p41
      FH429

<400> SEQUENCE: 23
```
tttttttttt tttttttttt ctgtgtgcac ggacaagaag                    40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Primer p41
      FH438

<400> SEQUENCE: 24
tttttttttt tttttttttt cggacaagaa gtggtgcgag                    40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Primer p41
      FH373

<400> SEQUENCE: 25
tttttttttt tttttttttt ctatatacga gggttttggt                    40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Primer p41
      FH440

<400> SEQUENCE: 26
tttttttttt tttttttttt gacaagaagt ggtgcgagac                    40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Primer p41
      FH549

<400> SEQUENCE: 27
tttttttttt tttttttttt ctctggtaaa tctgacgctt                    40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Primer p41
      FH615

<400> SEQUENCE: 28
tttttttttt tttttttttt cgtgacagag atgaatgaac                    40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Primer p41
      FH694

<400> SEQUENCE: 29

```
tttttttttt tttttttttt ctatctgcca aaaatttaca                              40
```

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Primer p41
      RH852

<400> SEQUENCE: 30

```
tttttttttt tttttttttt tttgagctgt tcctgagtta                              40
```

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Primer p41
      RH886

<400> SEQUENCE: 31

```
tttttttttt tttttttttt cttgtttacc cattcgttca                              40
```

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Primer p41
      RH854

<400> SEQUENCE: 32

```
tttttttttt tttttttttt tctttgagct gttcctgagt                              40
```

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Primer p41
      RH567

<400> SEQUENCE: 33

```
tttttttttt tttttttttt agcgtcagat ttaccagagc                              40
```

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Primer p41
      RH568

<400> SEQUENCE: 34

```
tttttttttt tttttttttt aagcgtcaga tttaccagag                              40
```

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Primer p41
      RH829

<400> SEQUENCE: 35

```
tttttttttt tttttttttt aggcttccac cgtcaacaac                              40
```

```
<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Primer p41
      RH830

<400> SEQUENCE: 36
tttttttttt tttttttttt aaggcttcca ccgtcaacaa                          40

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Primer p41
      RH598

<400> SEQUENCE: 37
tttttttttt tttttttttt gattaacctg tactataatg tgc                     43

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Primer p41
      RH598

<400> SEQUENCE: 38
tttttttttt tttttttttt cctgtactat aatgtgcgcc                         40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Primer p41
      RH562

<400> SEQUENCE: 39
tttttttttt tttttttttt cagatttacc agagcgttta                         40

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Primer HHV8
      FP1

<400> SEQUENCE: 40
tttttttttt tttttttttt atgcctgtgg attttcact                          39

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Primer
      HHV8RP1191

<400> SEQUENCE: 41
tttttttttt tttttttttt tcaaatcagg gggttaaatg                         40
```

-continued

```
<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Primer
      RHYb575

<400> SEQUENCE: 42
tgtcttctac ctactgctcc actaa                                            25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Primer
      HHYb544

<400> SEQUENCE: 43
aaagcgtctg gtaaatctga cgctt                                            25
```